(12) United States Patent
Andersen et al.

(10) Patent No.: US 8,257,427 B2
(45) Date of Patent: Sep. 4, 2012

(54) EXPANDABLE STENT

(75) Inventors: Erik Andersen, Roskilde (DK); Ning Wen, Chantilly (FR)

(73) Assignee: J.W. Medical Systems, Ltd., Weihai Shandong (CN)

( * ) Notice: Subject to any disclaimer, the term of this patent is extended or adjusted under 35 U.S.C. 154(b) by 422 days.

(21) Appl. No.: 12/481,792

(22) Filed: Jun. 10, 2009

(65) Prior Publication Data

US 2009/0248137 A1  Oct. 1, 2009

Related U.S. Application Data

(63) Continuation of application No. 10/489,181, filed as application No. PCT/EP02/09931 on Sep. 5, 2002, now abandoned.

(30) Foreign Application Priority Data

Sep. 11, 2001  (GB) .................................. 0121980.7
Apr. 16, 2002  (EP) .................................. 02252698

(51) Int. Cl.
*A61F 2/06* (2006.01)
(52) U.S. Cl. ................................... 623/1.15
(58) Field of Classification Search ......... 623/1.15–1.54
See application file for complete search history.

(56) References Cited

U.S. PATENT DOCUMENTS

| | | |
|---|---|---|
| 4,069,825 A | 1/1978 | Akiyama |
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |

(Continued)

FOREIGN PATENT DOCUMENTS

DE  1 953 1659   3/1997

(Continued)

OTHER PUBLICATIONS

European Search Report of EP Application No. 09159388.9, mailed Jul. 3, 2009, 5 pages total.

(Continued)

*Primary Examiner* — Gary Jackson
*Assistant Examiner* — Lindsey Bachman
(74) *Attorney, Agent, or Firm* — Kilpatrick, Townsend & Stockton LLP; Kenneth R. Shurtz, Esq.

(57) ABSTRACT

An expandable stent comprising a tubular body made up of a plurality of separated tubular elements (1) arranged along a common longitudinal axis. Each tubular element (1) comprises a plurality of rhombic-shaped closed cell elements (2) joined by circumferentially extending linking members (3). The closed cell elements (2) are expandable to allow the tubular elements, and hence the stent itself, to expand. In the direction of the longitudinal axis of the stent, the extremities of each of the closed cell elements has an enlarged loop (30) with waisted portions (33) which allow the tubular elements to interlock to create a stable structure, at least when in the unexpanded condition.

23 Claims, 17 Drawing Sheets

U.S. PATENT DOCUMENTS

| | | |
|---|---|---|
| 4,891,225 A | 1/1990 | Langer et al. |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,391,172 A | 2/1995 | Williams et al. |
| 5,421,955 A | 6/1995 | Lau et al. |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,531,735 A | 7/1996 | Thompson |
| 5,534,007 A | 7/1996 | St. Germain et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A | 1/1997 | Martinez et al. |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,997,563 A | 12/1999 | Kretzers et al. |
| 6,004,328 A | 12/1999 | Solar |
| 6,007,517 A | 12/1999 | Anderson |
| 6,022,359 A | 2/2000 | Frantzen |
| 6,022,374 A | 2/2000 | Imran |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duerig |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |

| Patent No. | Date | Inventor |
|---|---|---|
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,778,316 B2 | 8/2004 | Halas et al. |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,220,755 B2 | 5/2007 | Betts et al. |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,534,449 B2 | 5/2009 | Saltzman et al. |
| 8,016,870 B2 | 9/2011 | Chew et al. |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0037358 A1 | 3/2002 | Barry et al. |
| 2002/0052642 A1 | 5/2002 | Cox et al. |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Osypka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0168317 A1 | 11/2002 | Daighighian et al. |
| 2002/0177890 A1 | 11/2002 | Lenker |
| 2002/0183763 A1 | 12/2002 | Callol et al. |

| | | | | | | |
|---|---|---|---|---|---|---|
| 2002/0188343 A1 | 12/2002 | Mathis | | 2007/0088422 A1 | 4/2007 | Chew et al. |
| 2002/0188347 A1 | 12/2002 | Mathis | | 2007/0100423 A1 | 5/2007 | Acosta et al. |
| 2002/0193873 A1 | 12/2002 | Brucker et al. | | 2007/0100424 A1 | 5/2007 | Chew et al. |
| 2003/0045923 A1 | 3/2003 | Bashiri | | 2007/0106365 A1 | 5/2007 | Andreas et al. |
| 2003/0093143 A1 | 5/2003 | Zhao et al. | | 2007/0118202 A1 | 5/2007 | Chermoni |
| 2003/0097169 A1 | 5/2003 | Brucker et al. | | 2007/0118203 A1 | 5/2007 | Chermoni |
| 2003/0114912 A1 | 6/2003 | Sequin et al. | | 2007/0118204 A1 | 5/2007 | Chermoni |
| 2003/0114919 A1 | 6/2003 | McQuiston et al. | | 2007/0129733 A1 | 6/2007 | Will et al. |
| 2003/0114922 A1 | 6/2003 | Iwasaka et al. | | 2007/0135906 A1 | 6/2007 | Badylak et al. |
| 2003/0125791 A1 | 7/2003 | Sequin et al. | | 2007/0156225 A1 | 7/2007 | George et al. |
| 2003/0125800 A1 | 7/2003 | Shulze et al. | | 2007/0156226 A1 | 7/2007 | Chew et al. |
| 2003/0125802 A1 | 7/2003 | Callol et al. | | 2007/0179587 A1 | 8/2007 | Acosta et al. |
| 2003/0135259 A1 | 7/2003 | Simso | | 2007/0219612 A1 | 9/2007 | Andreas et al. |
| 2003/0135266 A1 | 7/2003 | Chew et al. | | 2007/0219613 A1 | 9/2007 | Kao et al. |
| 2003/0139796 A1 | 7/2003 | Sequin et al. | | 2007/0265637 A1 | 11/2007 | Andreas et al. |
| 2003/0139797 A1 | 7/2003 | Johnson et al. | | 2007/0270936 A1 | 11/2007 | Andreas et al. |
| 2003/0139798 A1 | 7/2003 | Brown et al. | | 2007/0276461 A1 | 11/2007 | Andreas et al. |
| 2003/0163085 A1 | 8/2003 | Tanner et al. | | 2007/0281117 A1 | 12/2007 | Kaplan et al. |
| 2003/0176909 A1 | 9/2003 | Kusleika | | 2007/0292518 A1 | 12/2007 | Ludwig |
| 2003/0191516 A1 | 10/2003 | Weldon et al. | | 2008/0004690 A1 | 1/2008 | Robaina |
| 2003/0195609 A1 | 10/2003 | Berenstein | | 2008/0046067 A1 | 2/2008 | Toyokawa |
| 2003/0199821 A1 | 10/2003 | Gerdts et al. | | 2008/0071345 A1 | 3/2008 | Hammersmark et al. |
| 2003/0204238 A1 | 10/2003 | Tedeschi | | 2008/0077229 A1 | 3/2008 | Andreas et al. |
| 2003/0208223 A1 | 11/2003 | Kleiner | | 2008/0091257 A1 | 4/2008 | Andreas et al. |
| 2003/0212447 A1 | 11/2003 | Euteneuer | | 2008/0097299 A1 | 4/2008 | Andreas et al. |
| 2003/0225446 A1 | 12/2003 | Hartley | | 2008/0097574 A1 | 4/2008 | Andreas et al. |
| 2004/0024450 A1 | 2/2004 | Shulze et al. | | 2008/0125850 A1 | 5/2008 | Andreas et al. |
| 2004/0030380 A1 | 2/2004 | Shulze et al. | | 2008/0132989 A1 | 6/2008 | Snow et al. |
| 2004/0044395 A1 | 3/2004 | Nelson | | 2008/0147162 A1 | 6/2008 | Andreas et al. |
| 2004/0073290 A1 | 4/2004 | Chouinard | | 2008/0177369 A1 | 7/2008 | Will et al. |
| 2004/0093061 A1 | 5/2004 | Acosta et al. | | 2008/0199510 A1 | 8/2008 | Ruane et al. |
| 2004/0093067 A1 | 5/2004 | Israel | | 2008/0208311 A1 | 8/2008 | Kao et al. |
| 2004/0106979 A1 | 6/2004 | Goicoechea | | 2008/0208318 A1 | 8/2008 | Kao et al. |
| 2004/0111145 A1 | 6/2004 | Serino et al. | | 2008/0234795 A1 | 9/2008 | Snow et al. |
| 2004/0117008 A1 | 6/2004 | Wnendt et al. | | 2008/0234798 A1 | 9/2008 | Chew et al. |
| 2004/0143322 A1 | 7/2004 | Litvack et al. | | 2008/0234799 A1 | 9/2008 | Acosta et al. |
| 2004/0176832 A1 | 9/2004 | Hartley et al. | | 2008/0243225 A1 | 10/2008 | Satasiya et al. |
| 2004/0181239 A1 | 9/2004 | Dorn et al. | | 2008/0249607 A1 | 10/2008 | Webster et al. |
| 2004/0186551 A1 | 9/2004 | Kao et al. | | 2008/0269865 A1 | 10/2008 | Snow et al. |
| 2004/0193245 A1 | 9/2004 | Deem et al. | | 2009/0076584 A1 | 3/2009 | Mao et al. |
| 2004/0215312 A1 | 10/2004 | Andreas et al. | | 2009/0105686 A1 | 4/2009 | Snow et al. |
| 2004/0230285 A1 | 11/2004 | Gifford, III et al. | | 2009/0149863 A1 | 6/2009 | Andreas et al. |
| 2004/0243217 A1 | 12/2004 | Andersen et al. | | 2009/0228088 A1 | 9/2009 | Lowe |
| 2004/0249434 A1 | 12/2004 | Andreas et al. | | 2009/0234428 A1 | 9/2009 | Snow et al. |
| 2005/0010276 A1 | 1/2005 | Acosta et al. | | 2009/0264979 A1 | 10/2009 | Kao et al. |
| 2005/0038494 A1 | 2/2005 | Eidenschink | | 2010/0004729 A1 | 1/2010 | Chew et al. |
| 2005/0038505 A1 | 2/2005 | Shulze et al. | | | | |
| 2005/0049673 A1 | 3/2005 | Andreas et al. | | FOREIGN PATENT DOCUMENTS | | |
| 2005/0080474 A1 | 4/2005 | Andreas et al. | | | | |
| 2005/0080475 A1 | 4/2005 | Andreas et al. | | DE | 196 30 469 | 1/1998 |
| 2005/0085897 A1 | 4/2005 | Bonsignore | | DE | 199 50 756 | 8/2000 |
| 2005/0090846 A1 | 4/2005 | Pedersen et al. | | DE | 101 03 000 | 8/2002 |
| 2005/0125051 A1 | 6/2005 | Eidenschink et al. | | EP | 0 203 945 B2 | 12/1986 |
| 2005/0131008 A1 | 6/2005 | Betts et al. | | EP | 0 274 129 B1 | 7/1988 |
| 2005/0143827 A1 | 6/2005 | Globerman et al. | | EP | 0 282 143 | 9/1988 |
| 2005/0165378 A1 | 7/2005 | Heinrich et al. | | EP | 0 505 686 | 9/1992 |
| 2005/0209674 A1 | 9/2005 | Kutscher et al. | | EP | 0 533 960 | 3/1993 |
| 2005/0222671 A1 | 10/2005 | Schaeffer et al. | | EP | 0 596 145 | 5/1994 |
| 2005/0228477 A1 | 10/2005 | Grainger et al. | | EP | 0 714 640 | 6/1996 |
| 2005/0245637 A1 | 11/2005 | Hossainy et al. | | EP | 0 947 180 | 10/1999 |
| 2005/0288764 A1 | 12/2005 | Snow et al. | | EP | 1 258 230 | 11/2002 |
| 2005/0288766 A1 | 12/2005 | Plain et al. | | EP | 1 266 638 B1 | 12/2002 |
| 2006/0069424 A1 | 3/2006 | Acosta et al. | | EP | 1 277 449 | 1/2003 |
| 2006/0173529 A1 | 8/2006 | Blank | | EP | 1 290 987 A2 | 3/2003 |
| 2006/0200223 A1 | 9/2006 | Andreas et al. | | EP | 1 318 765 | 6/2003 |
| 2006/0206190 A1 | 9/2006 | Chermoni | | EP | 1 523 959 A2 | 4/2005 |
| 2006/0229700 A1 | 10/2006 | Acosta et al. | | EP | 1 523 960 A2 | 4/2005 |
| 2006/0229706 A1 | 10/2006 | Shulze et al. | | GB | 2277875 A | 11/1994 |
| 2006/0271150 A1 | 11/2006 | Andreas et al. | | JP | 03-133446 | 6/1991 |
| 2006/0271151 A1 | 11/2006 | McGarry et al. | | JP | 10-503663 | 4/1998 |
| 2006/0282147 A1 | 12/2006 | Andreas et al. | | JP | 10-295823 | 11/1998 |
| 2006/0282149 A1 | 12/2006 | Kao | | JP | 2000-516486 A | 12/2000 |
| 2006/0282150 A1 | 12/2006 | Olson et al. | | JP | 2001-190687 | 7/2001 |
| 2006/0287726 A1 | 12/2006 | Segal et al. | | JP | 2004-121343 A | 4/2004 |
| 2007/0027521 A1 | 2/2007 | Andreas et al. | | WO | WO 95/26695 A2 | 10/1995 |
| 2007/0043419 A1 | 2/2007 | Nikolchev et al. | | WO | WO 95/29647 | 11/1995 |
| 2007/0067012 A1 | 3/2007 | George et al. | | WO | WO 96/26689 | 9/1996 |
| 2007/0088368 A1 | 4/2007 | Acosta et al. | | WO | WO 96/33677 | 10/1996 |
| 2007/0088420 A1 | 4/2007 | Andreas et al. | | WO | WO 96/39077 | 12/1996 |
| | | | | WO | WO 97/46174 | 12/1997 |

| | | |
|---|---|---|
| WO | WO 97/48351 | 12/1997 |
| WO | WO 98/05270 A1 | 2/1998 |
| WO | WO 98/20810 | 5/1998 |
| WO | WO 98/37833 | 9/1998 |
| WO | WO 98/58600 | 12/1998 |
| WO | WO 99/01087 | 1/1999 |
| WO | WO 99/65421 | 12/1999 |
| WO | WO 00/12832 A3 | 3/2000 |
| WO | WO 00/15151 | 3/2000 |
| WO | WO 00/25841 | 5/2000 |
| WO | WO 00/32136 | 6/2000 |
| WO | WO 00/41649 | 7/2000 |
| WO | WO 00/50116 | 8/2000 |
| WO | WO 00/56237 | 9/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | WO 2005/009295 | 2/2005 |
| WO | WO 2005/013853 | 2/2005 |
| WO | WO 2006/036939 | 4/2006 |
| WO | WO 2006/047520 | 5/2006 |
| WO | WO 2007/035805 | 3/2007 |
| WO | WO 2007/053187 | 5/2007 |
| WO | WO 2007/146411 | 12/2007 |
| WO | WO 2008/005111 | 1/2008 |

OTHER PUBLICATIONS

Examination Report of EP Application No. 09159388.9, mailed Jun. 18, 2010, 4 pages total.

European Search Report of EP Patent Application No. 09159388.9, mailed Jul. 3, 2009, 5 pages total.

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13, XP00976354.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; abandoned.

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 10/874,859, filed Jun. 22, 2004, first named inventor: Pablo Acosta. Abandoned.

Notice of the Reason for Refusal for Japanese Application No. 2009-142782 mailed Aug. 16, 2011.

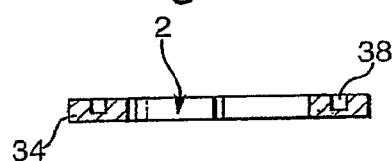
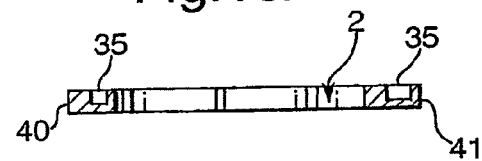
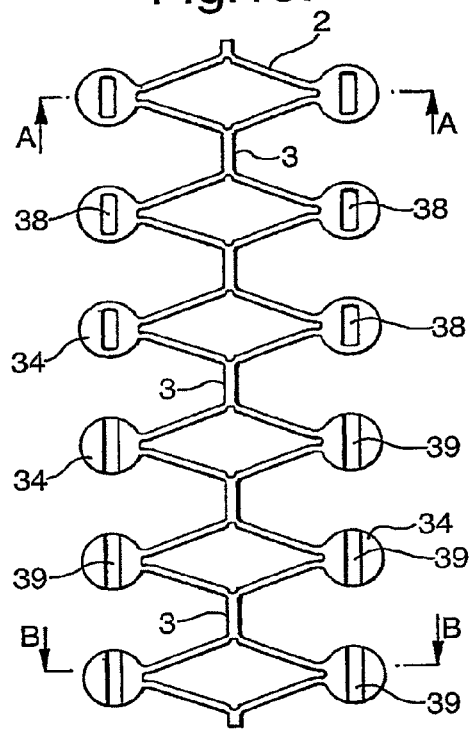
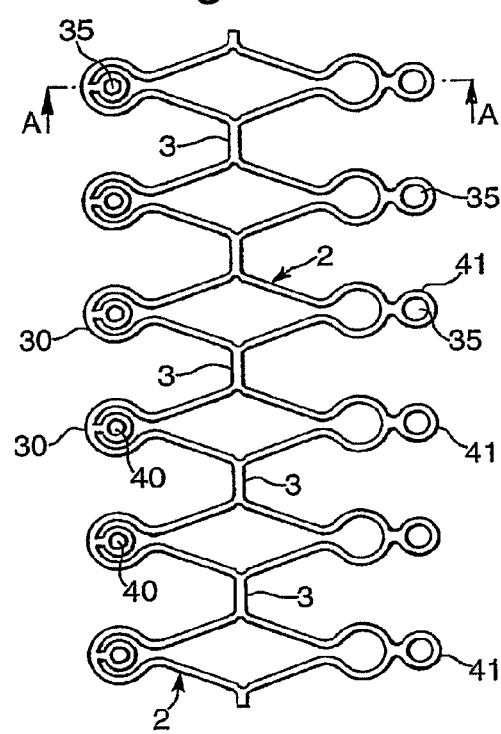

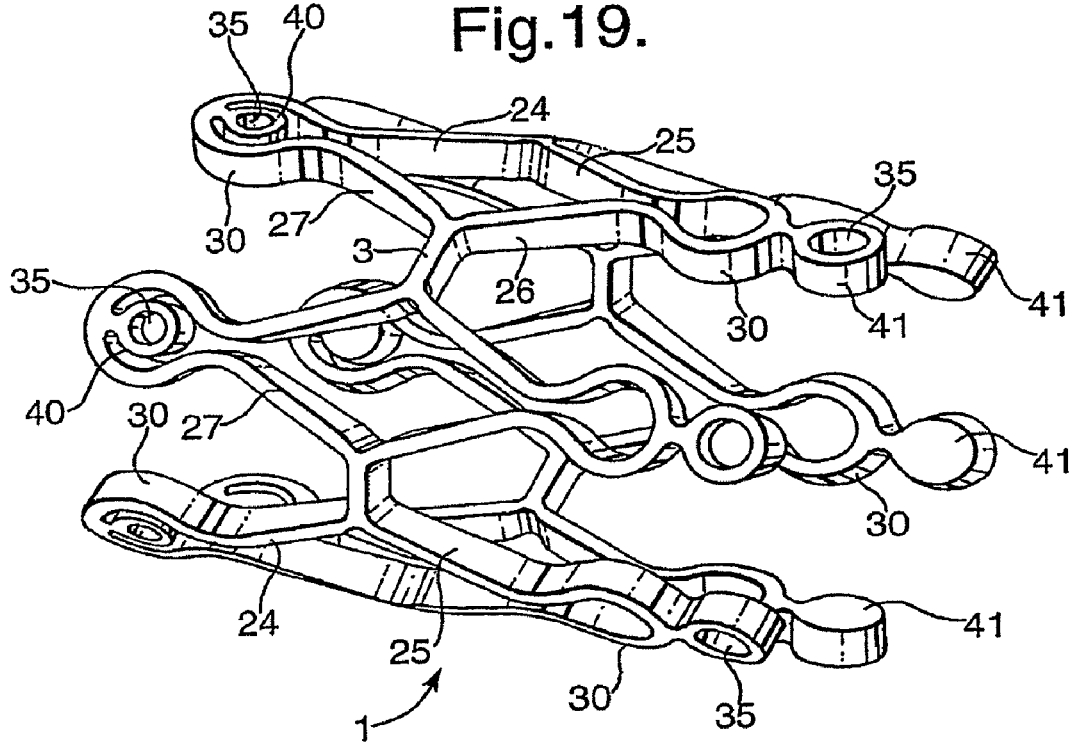

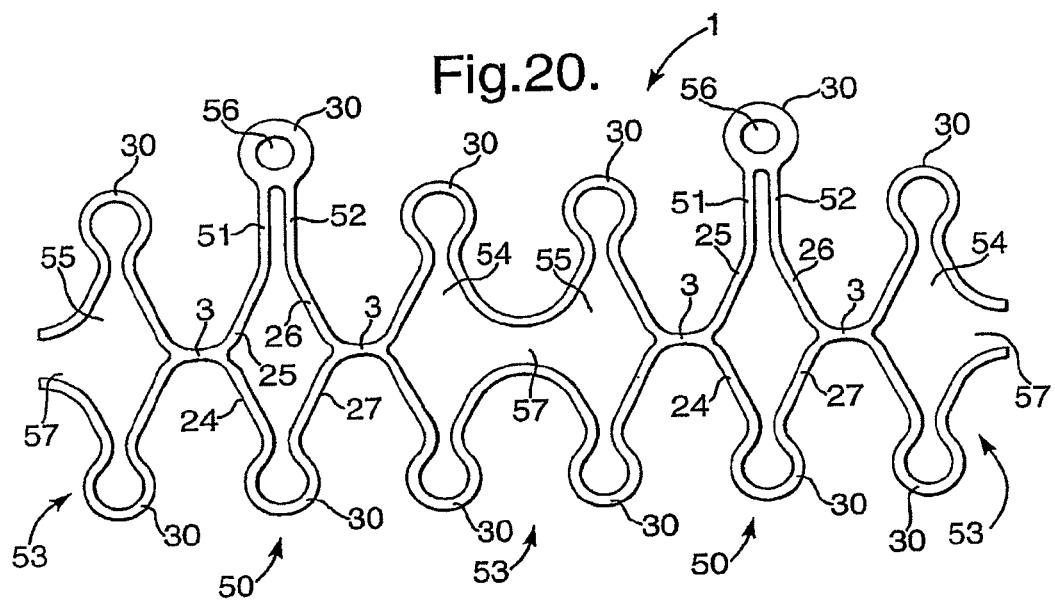
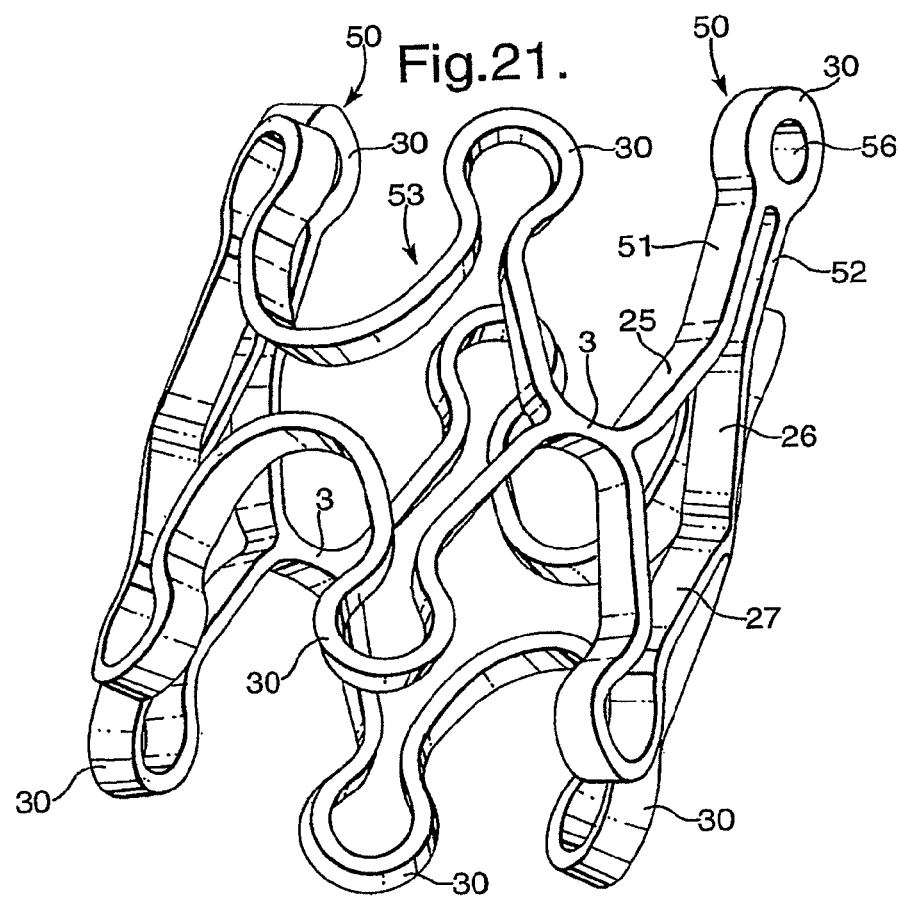

EXPANDABLE STENT

CROSS-REFERENCES TO RELATED APPLICATIONS

The present application is a continuation of U.S. patent application Ser. No. 10/489,181 filed Mar. 10, 2004, now abandoned, which is a National Stage Entry of PCT Application No. PCT/EP02/09931, filed Sep. 5, 2002, which claims priority to both European Patent Application No. 02252698.2, filed Apr. 16, 2002, and British Patent Application No. 0121980.7, filed Sep. 11, 2001. The entire contents of each of the above patent applications is fully incorporated herein by reference.

This invention relates to an expandable tubular stent for implantation in the lumen of a body duct in order to ensure a passage therein.

Such stents are used mainly in the treatment of blood vessels exhibiting stenoses, and more generally in the treatment of diseases of various anatomical ducts of the human or animal body, such as, for example, the urinary ducts, especially the urethra, or the digestive ducts, especially the esophagus.

The percutaneous implantation of an expandable tubular stent in a stenotic blood vessel is generally recommended, for example after a conventional angioplasty procedure, for preventing the dilated vessel from closing up again spontaneously or for preventing its occlusion by the formation of a new atheromatous plaque and the possible recurrence of stenosis.

A known type of expandable tubular stent consists of an assembly of radially expandable, tubular elements aligned along a common longitudinal axis and successively joined together in pairs by respective sets of linking members. Such a stent is disclosed, for example, in international patent application WO 98/58600 in which each of the tubular elements consists of a strip forming a zigzag corrugation defining bent extreme portions which are successively connected together in pairs in opposite directions by rectilinear intermediate portions. By virtue of this zigzag corrugation, the stent is expandable between a first, unexpanded state, enabling it to be implanted percutaneously by means of an insertion device of reduced diameter, and a second, expanded state, in which the stent makes it possible to ensure a passage in the lumen of the body duct. Stents of this type are also disclosed in international patent applications WO 96/26689 and WO 98/20810.

To install the stent, it is placed in the unexpanded state on an angioplasty balloon catheter. Once in place, the balloon is inflated in order to cause the stent to expand. Alternatively, the stent may be made from a material which has a recovery capacity, so that the stent may automatically expand, once in place.

According to the invention there is provided a stent comprising a tubular body made up of a plurality of separate, radially expandable, tubular elements aligned along a common longitudinal axis, wherein at least some of the tubular elements each comprise a plurality of closed cell elements, each joined to the next by a circumferentially-extending linking member.

It will thus be seen that each tubular element comprises a closed loop consisting of a series of alternating closed cell elements and circumferential linking members.

In most known stents, the tubular elements are physically linked to one another by longitudinally extending linking members. One or more of such longitudinally extending linking members may link each pair of adjacent tubular elements. However, there are a number of advantages to be obtained by not using longitudinally-extending linking members, so that the stent consists simply of a collection of separate tubular members whose alignment along a common axis to form the stent is achieved by other means. Preferably the tubular elements, as well as being expandable, are also compressible.

By "separate" is meant that the tubular elements are not directly connected together by longitudinally-extending linking members. The word "separate" does not imply that the elements may not touch and, as will be explained below, in certain conditions of the stent, the linking members will touch and will indeed link together. In the absence of longitudinally-extending linking members, the structural integrity of the stent is realised by alternative means, such as:

1) A tubular member or framework which is not directly joined to the adjacent tubular elements but over which or within which the tubular elements are positioned in the desired alignment. For example, the balloon which is used to expand the stent can be used to maintain the position of the tubular members with respect to one another.

2) Interlock means which mechanically holds the tubular members together even though they are not directly joined. An example of this would be to provide co-operating interlock means on the tubular elements themselves.

In an embodiment of the invention, both these techniques are employed: the tubular elements are placed over the balloon and interlocked together so that the stent remains structurally stable during its often tortuous passage to the treatment site. Upon expansion, the interlocking is released, and the balloon alone then maintains the positional stability of the stent components. After the balloon has been deflated, the expanded stent, which has undergone plastic deformation, maintains its expanded shape and thus keeps the vessel being treated at its desired diameter. The expanded vessel applies a reaction force, due to its elastic nature, against the stent and thus maintains the position of the individual tubular elements making up the stent with respect to one another.

In order to allow the stent to expand it is necessary that the tubular elements be radially expandable. For this purpose, each tubular element is constructed in such a way that it is expandable in the circumferential direction. This may be achieved by the closed cell construction of the invention in which the expansion capabilities of the tubular elements are contained wholly or primarily in the closed cell elements. To avoid out of balance forces during expansion, it is preferred that the closed cell elements be positioned symmetrically with respect to the circumferential linking members, but asymmetric arrangements are also possible.

The tubular elements making up the stent may be all identical, or they may be different—for example, a stent could be made up of a combination of tubular elements comprising closed cell elements, and tubular elements constructed in some other way, arranged to create particular desired properties of the stent as a whole.

The circumferential linking members may simply consist of rectilinear members extending in the circumferential direction. Alternatively the circumferential linking members may be angled to the circumferential direction, so long as they have a component in the circumferential direction so that the adjacent closed cell elements are spaced apart in the circumferential direction. In a further alternative, the circumferential linking members are not rectilinear, but are some other shape to create particular desired characteristics—for example, the circumferential linking members could be such as to provide a degree of flexibility in the circumferential direction, although the expansion capabilities of the tubular element will still be primarily due to the closed cell elements. Preferably, all of the circumferential linking members are the same length in the circumferential direction so that the closed cell elements are evenly distributed about the circumference of the tubular element.

The circumferential linking members attach to the closed cell elements at respective spaced attachment points, and each closed cell element is constructed in such a way that it is capable of expanding from a first position in which the attachment points are relatively close together to a second position in which the attachment points are relatively further apart. In this way, the circumferential length of the tubular element can be increased from a relatively low value, corresponding to the unexpanded condition of the stent, to a relatively higher value, corresponding to the expanded condition of the stent. In one possible construction, each closed cell element comprises two individual members extending between said attachment points, said members being spaced apart in the direction of the longitudinal axis of the stent. Thus, one of said members may be said to be the proximal member, the other the distal member. The proximal and distal members are preferably symmetrically arranged about a straight line joining the two attachment points, this line being coaxial around the circumference with the general direction of the circumferential linking members.

The proximal and distal members are capable of bending in order to enable the expansion of the closed cell element from the first position to the second position. This may be achieved in various ways. For example, each of the proximal and distal members may be fabricated from a flexible member which is thus able to bend to accommodate the required movement. Alternatively, each of the proximal and distal members is fabricated by a plurality of relatively rigid side members joined by hinge members. In the preferred embodiment, each of the proximal and distal members comprises two such side members joined together by a hinge. Preferably the two side members are of equal length, but they do not need to be; however, for a symmetric construction the corresponding side members in each of the proximal and distal members should be of equal length.

In an embodiment, each closed cell element has a generally rhombic or diamond shape, comprising four side members of relatively stiff construction, joined by four hinge members corresponding to the corners of the rhombus. The circumferential linking members attach to the closed cell element at the location of opposite hinge members. Thus, each circumferential linking member has, at one end, one of the hinge members of one closed cell element and, at the opposite end, the opposite hinge member of the adjacent closed cell element.

It is not essential that all the closed cell elements in each tubular element are the same shape. In an alternative embodiment every other closed cell element is of rhombic shape, as described above, whilst the closed cell elements in between comprise "double rhombic" elements, each comprising two rhombic shapes, as described above, aligned in the circumferential direction, but joined by a narrow, but not closed, neck portion.

Other arrangements of closed cell elements are possible, according to the circumstances.

The aforesaid interlock means can conveniently be provided by providing an enlarged portion at each of the hinge members to which the link members are not attached. The narrowing side members as they approach each hinge member, together with the respective enlarged portion, form a narrow or waist portion which can overlap with an enlarged portion from the next adjacent tubular element. Two such waist portions acting together can thus retain an enlarged portion from the next adjacent tubular element.

The interlock means do not have to be provided on every closed cell element. It may be adequate to provide them on just a few closed cell elements, but evenly spaced about the circumference, so as to give a balanced attachment between adjacent tubular elements. For this purpose some of the closed cell elements may extend further in the axial direction of the stent than the remaining closed cell elements, so that these extended portions may interlink with the adjacent tubular element.

This enlarged portion can be formed as a flexible open cell with a narrowed neck, or can be formed as a relatively rigid block, from which, for example, the two side members may emerge via a respective narrowed portion to act as a hinge—in this latter case, the hinge member actually consists of two separate hinges.

In current medical practice, it is often the case that, in addition to its role in providing ongoing support for the vessel wall, the stent is required to act as a means whereby therapeutic agents may conveniently be applied. Indeed the trauma caused during the angioplasty procedure may call for localised drug treatment. In addition, drugs may be used to counteract restenosis, and for other purposes. Conventionally, such therapeutic agents are contained within some form of coating which is applied to the stent so that the drug will be released over a period of time. One problem with such an arrangement, however, is that, whereas the drug needs primarily to be applied through the wall of the vessel being treated, in practice as much of the drug is released into the fluid, e.g. blood, flowing within the vessel as passes through the vessel wall. Not only is the drug which is washed away effectively wasted, it can also do positive harm elsewhere if, for example, it enters a sensitive organ such as the heart.

Thus, in an embodiment of the invention the stent is equipped with wells opening into its exterior surface—that surface which, when the stent is in place, will face the wall of the vessel being treated—said wells being suitable to contain therapeutic agent.

The wells may comprise holes or grooves opening into the exterior surface of the stent, and may or may not pass right through the material of the stent to the interior of the stent. However, if the wells pass through to the interior of the stent there is clearly a danger of at least some of the drug being released into the fluid flowing within the vessel. Therefore it is preferred that, in such a case, that end of the well which opens into the interior of the stent is constructed, for example by being made narrower, and/or being plugged by a material which prevents or considerably reduces the tendency of the therapeutic agent to flow therethrough.

Thus it is preferred that the well is wholly or primarily open to the exterior surface of the stent so that the therapeutic agent may act directly on the wall of the vessel and does not get washed away by the fluid flowing along the vessel being treated.

The wells may open onto any suitable exterior surface of the stent. For example, the wells may conveniently be formed in the blocks which form the enlarged portions of the closed cell elements. For example, each block could be formed with a well in the form of a hole, which may or may not be a through hole and which opens into that surface of the block which forms part of the exterior surface of the stent. Alternatively the wells may be formed as grooves in the side members of the closed cell elements, the grooves opening into that surface of the side members which forms part of the exterior surface of the stent. It will be understood, however, that the above positions are given just as examples.

As mentioned above, the wells contain therapeutic agents which are intended to be released at a controlled rate against the wall of the vessel being treated. Not all of the wells necessarily will contain the therapeutic agent, and not all wells need to contain the same therapeutic agent. It is possible, for example, that the wells of different tubular elements contain different therapeutic agent, opening up the possibility of providing mixtures of drugs by choosing particular tubular elements carrying particular drugs to make up the stent. Clearly this is particularly easy with a stent in which the tubular elements are separate from one another. The therapeutic agents may also be provided in separate layers within the well, with the drug needed first being in the top layer, and the drugs needed later in lower layers, in correct sequence.

In addition, it is possible to provide that some of the wells contain therapeutic agents which have different rates of release. For example the drug contained in the wells of those tubular elements at or near the ends of the stent could be arranged to have a more rapid or a slower release rate than the remainder.

The therapeutic agents may be provided in any suitable form for retention in the wells, and for sustained release, once installed within the vessel. Examples are liquid, gel or powder form.

In order that the invention may be better understood, several embodiments thereof will now be described by way of example only and with reference to the accompanying drawings in which.

Figure 1:
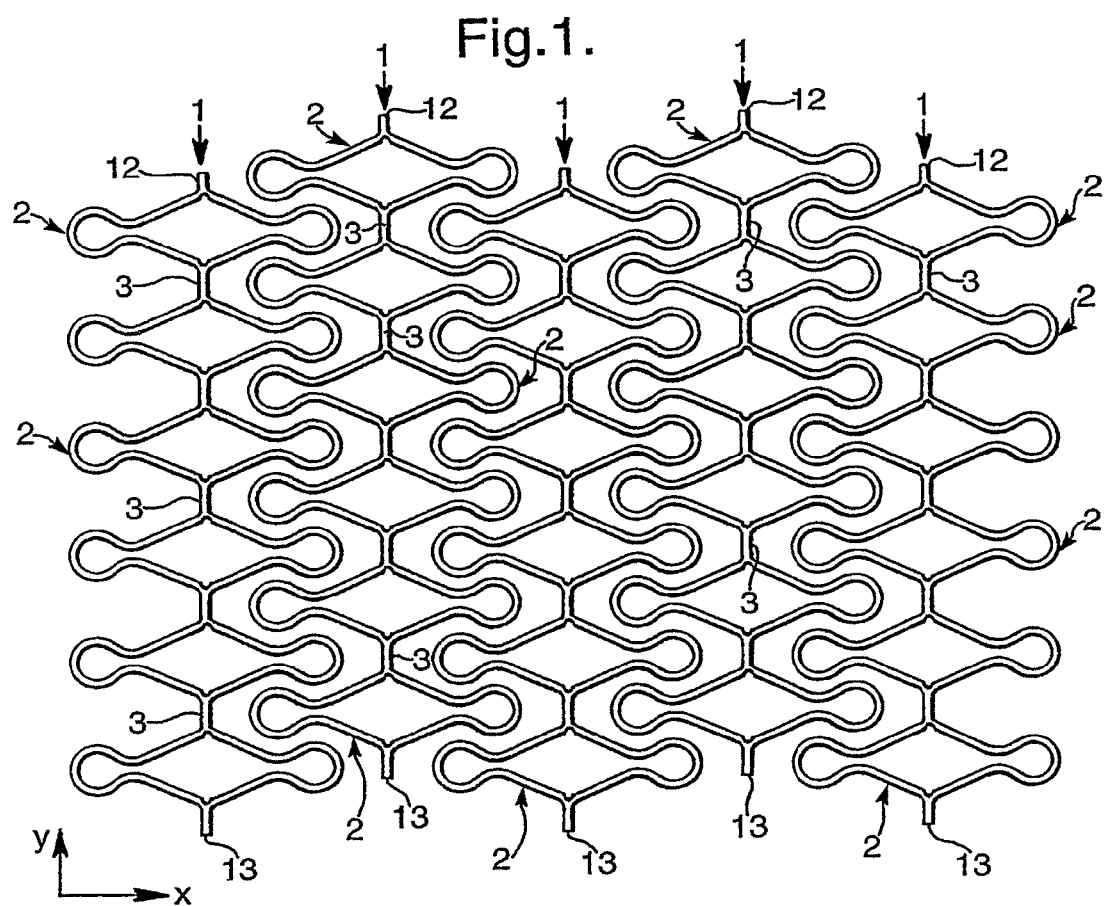
FIG. 1 is a two-dimensional view of the evolute of the surface of a stent according to a first aspect of the present invention, in its "as cut" condition.
Figure 2:
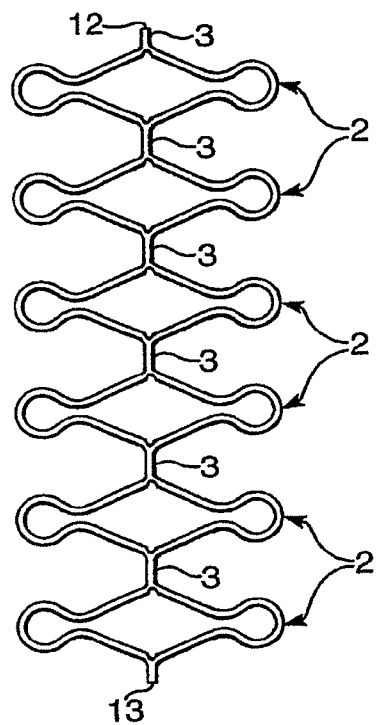
FIG. 2 is a view corresponding to FIG. 1, but showing just a single tubular element.
Figure 4A:
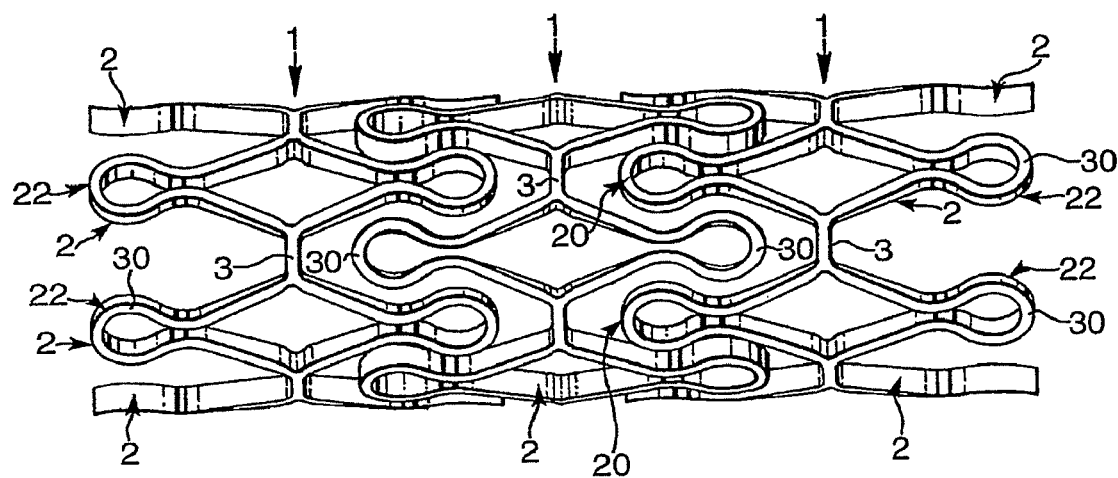
Figure 4B:
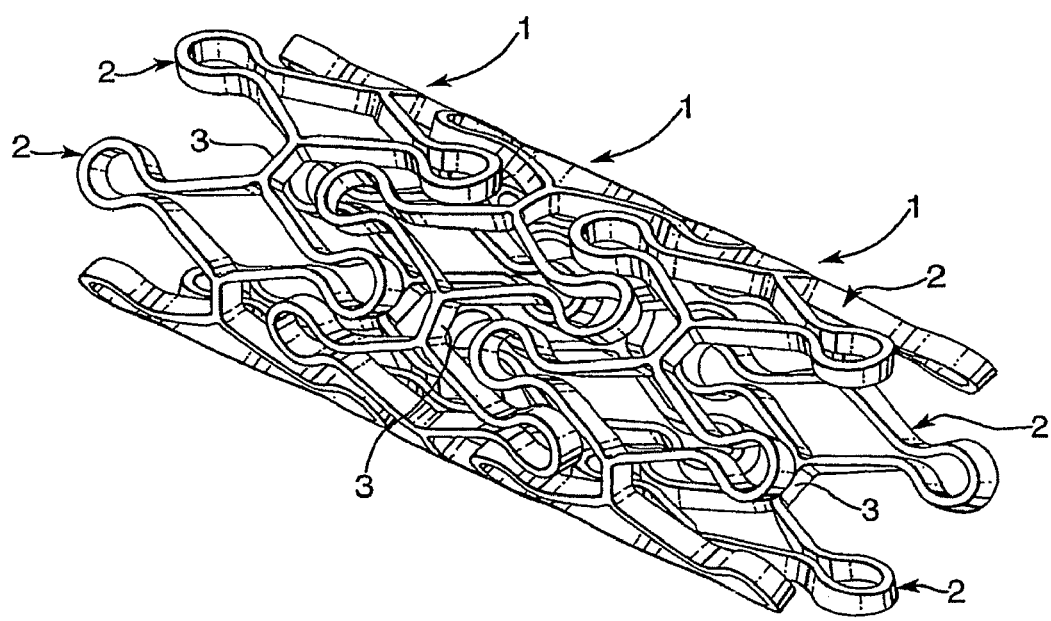
Figure 5:
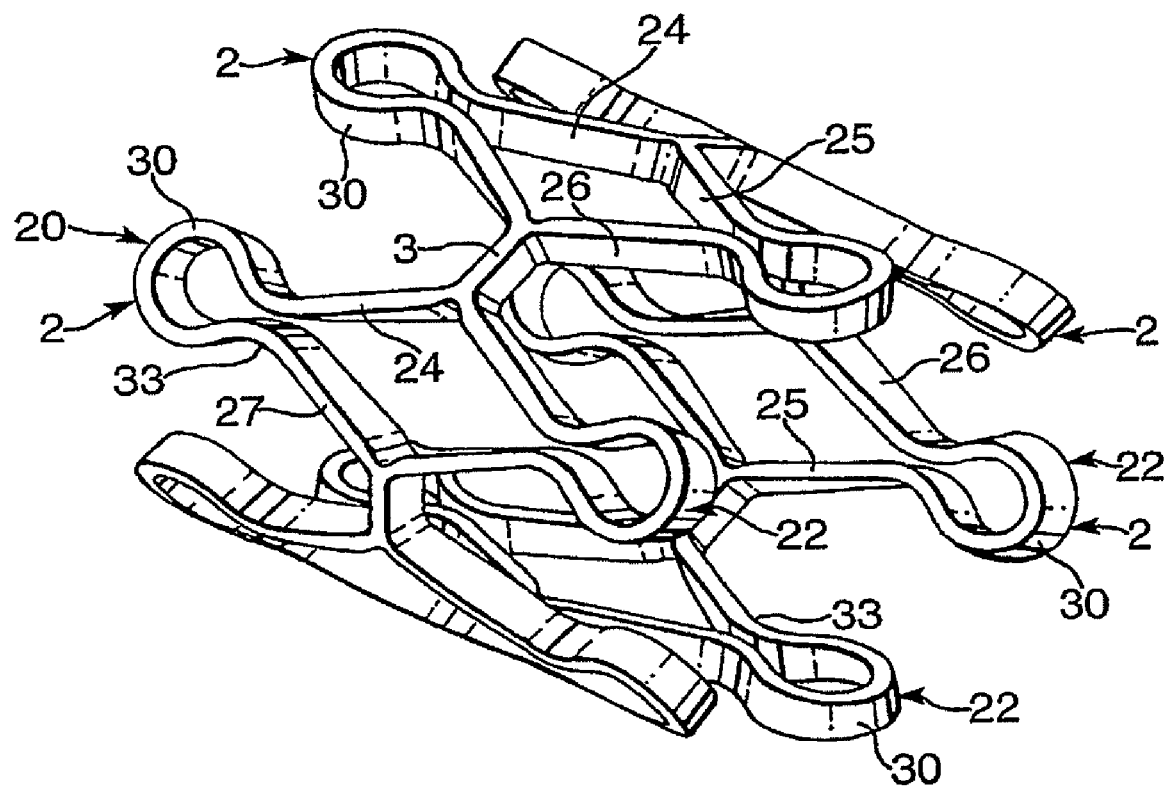
Figure 6:
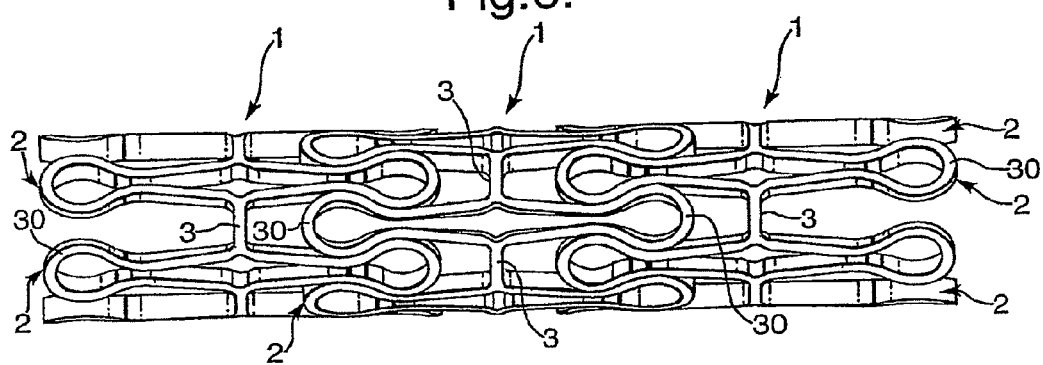
Figure 7:
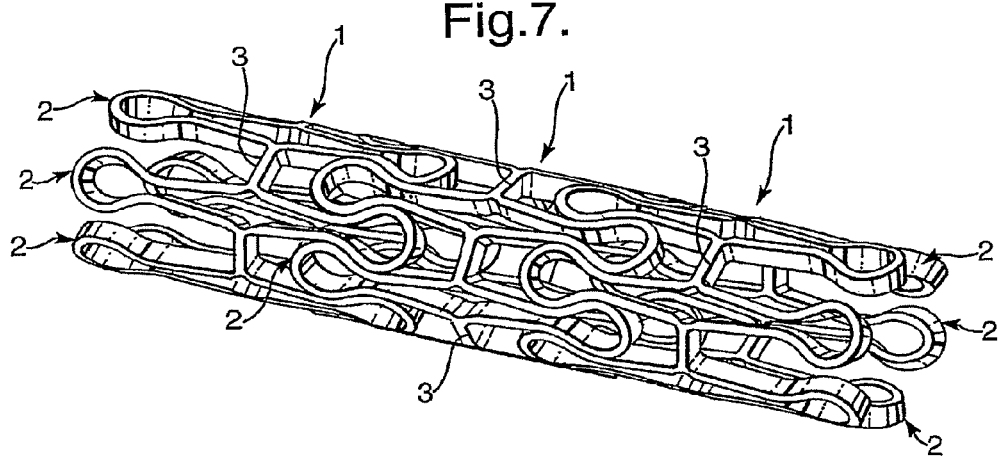
Figure 8:
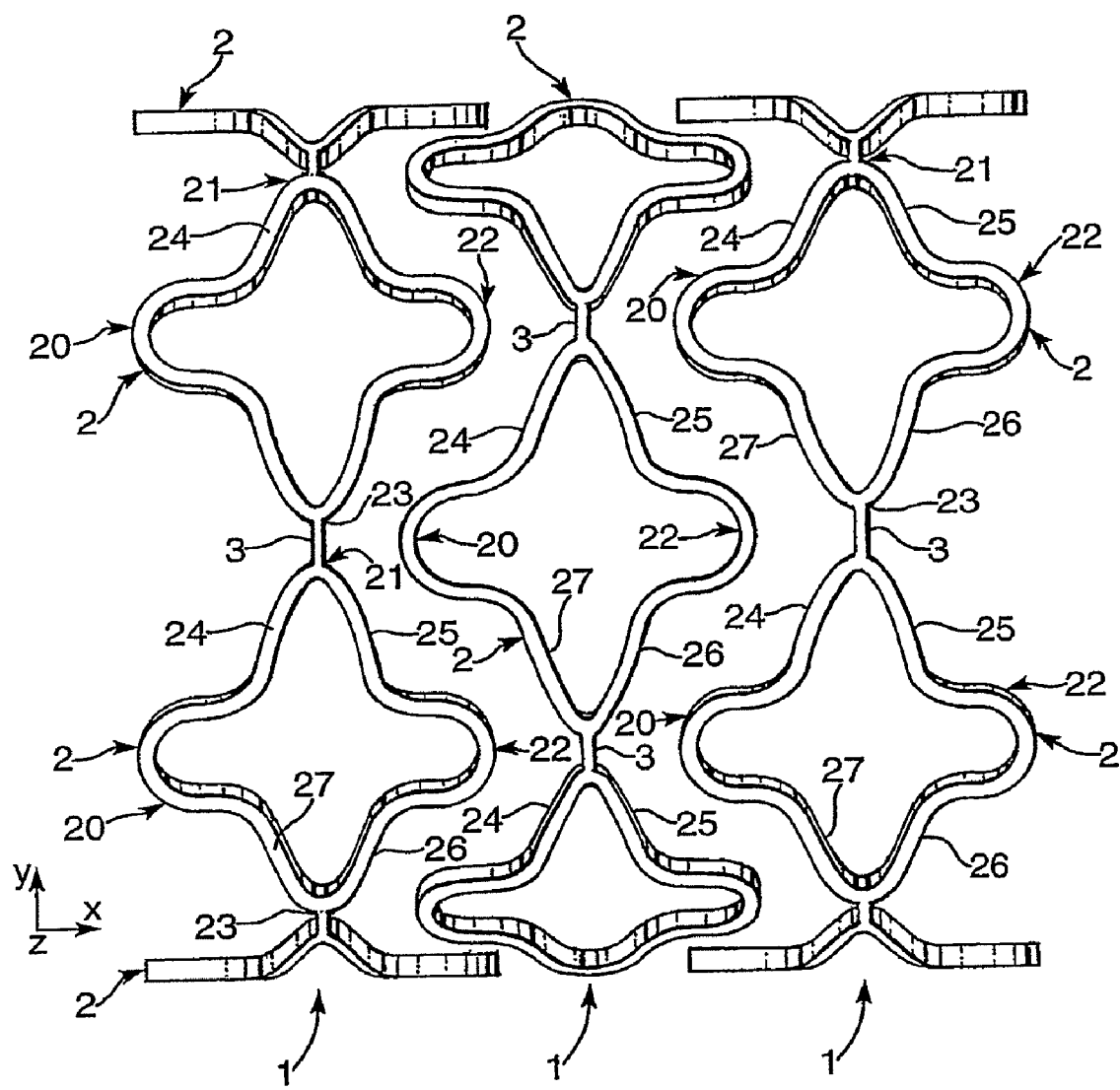
Figure 9:
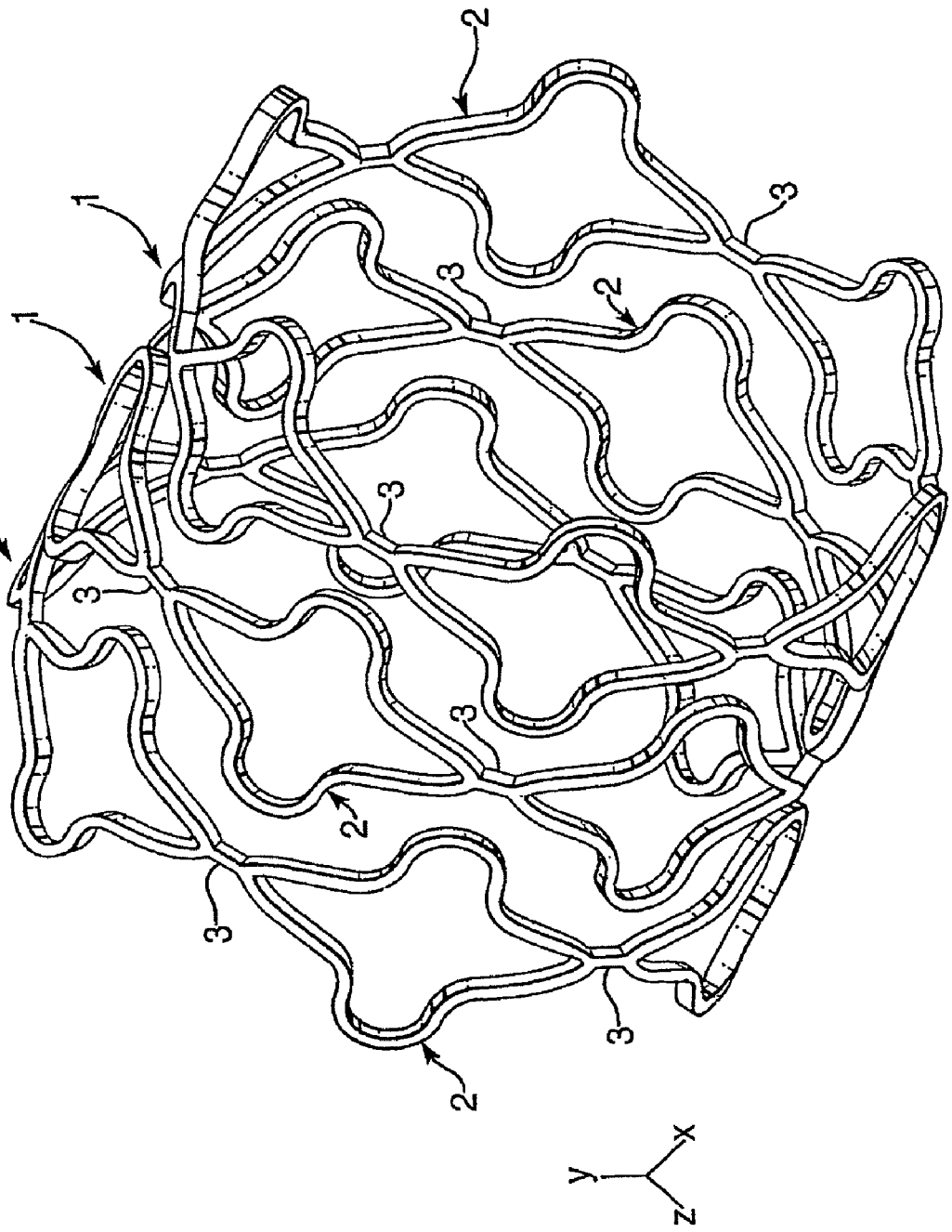
Figure 10:
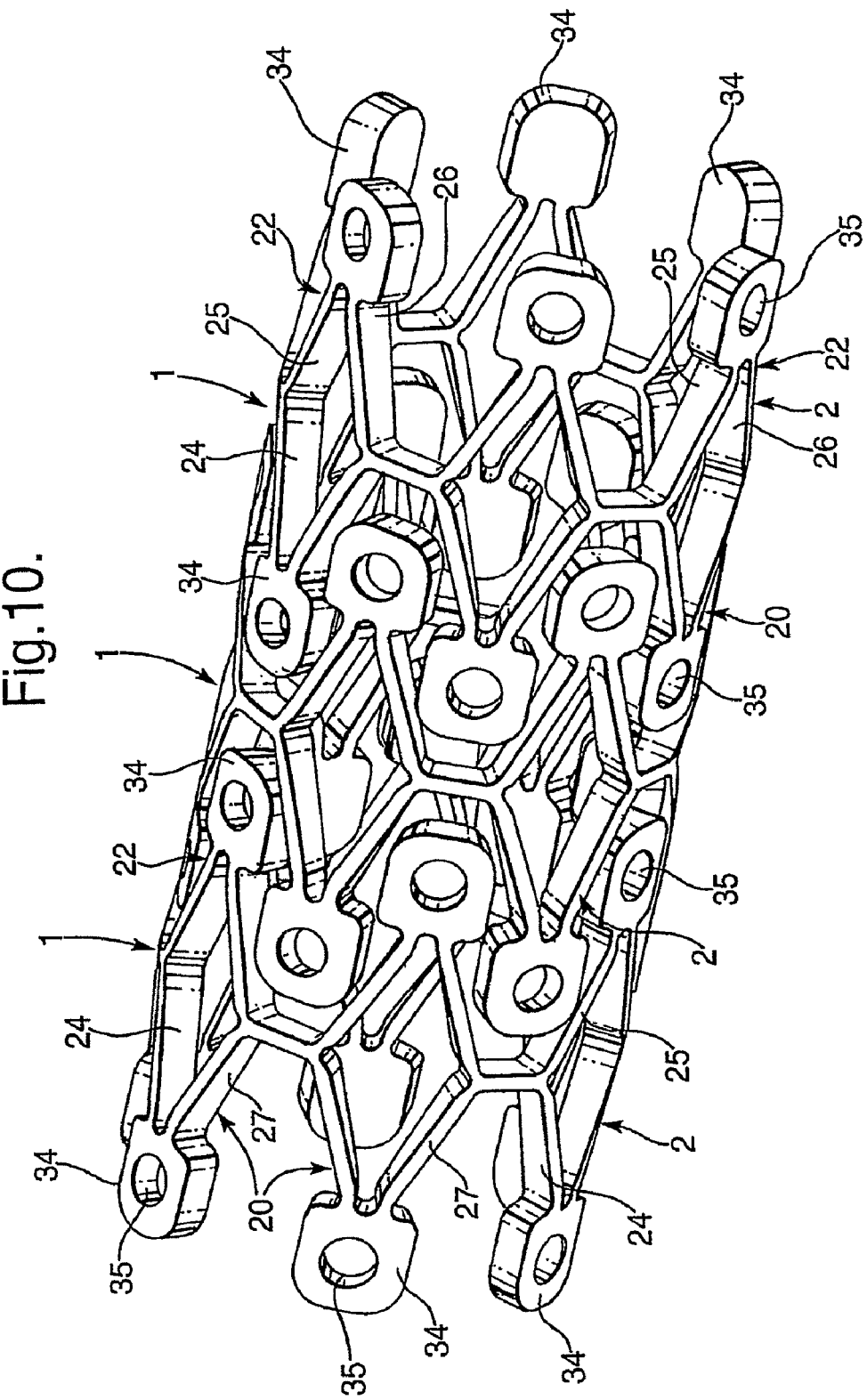
Figure 11:
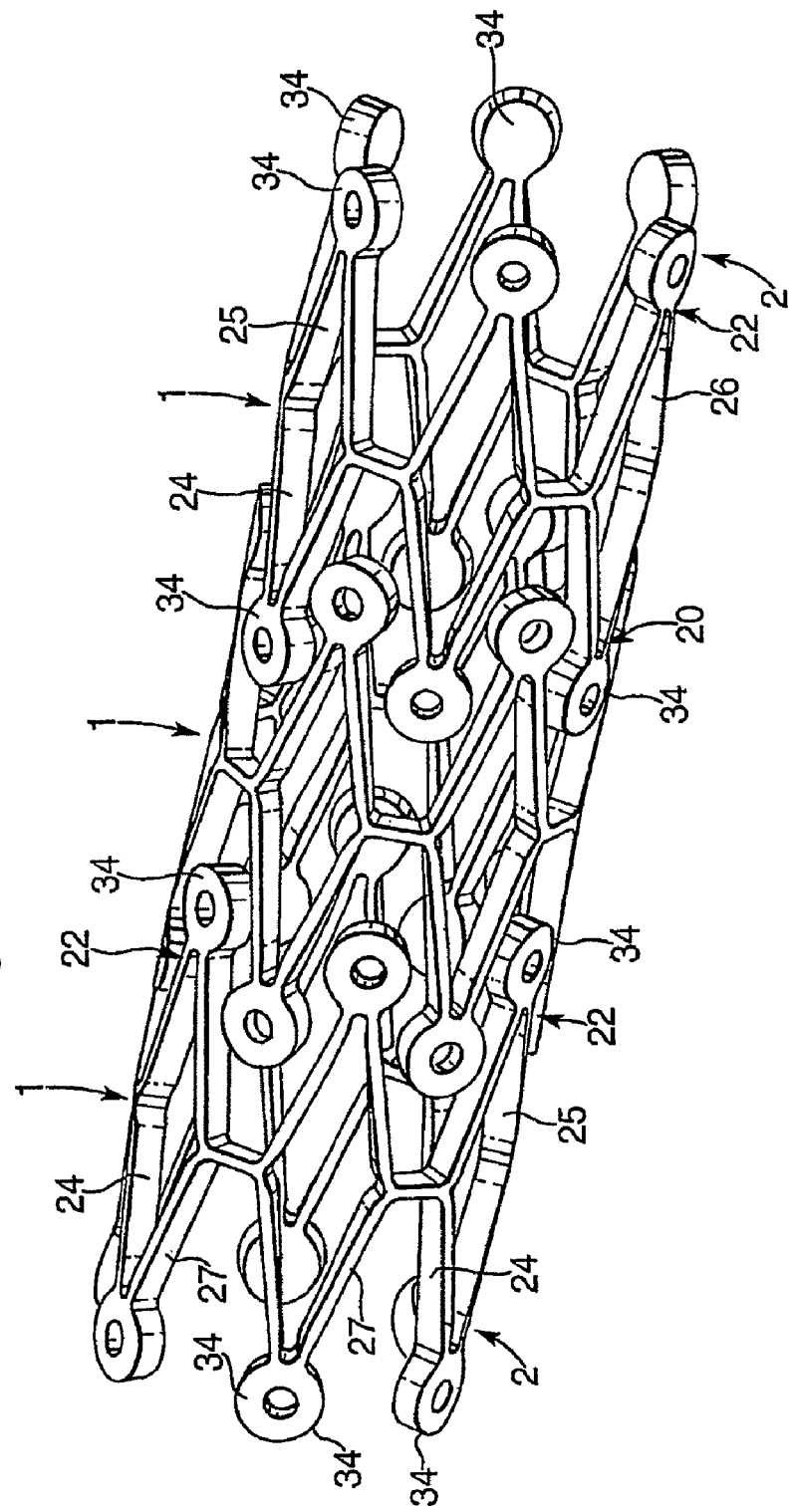
Figure 12A:
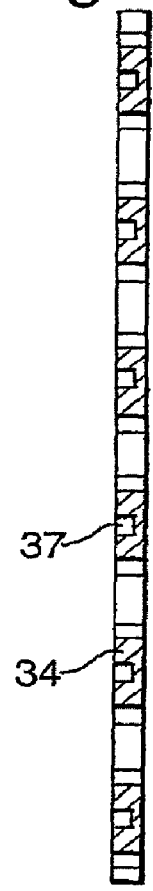
Figure 12:
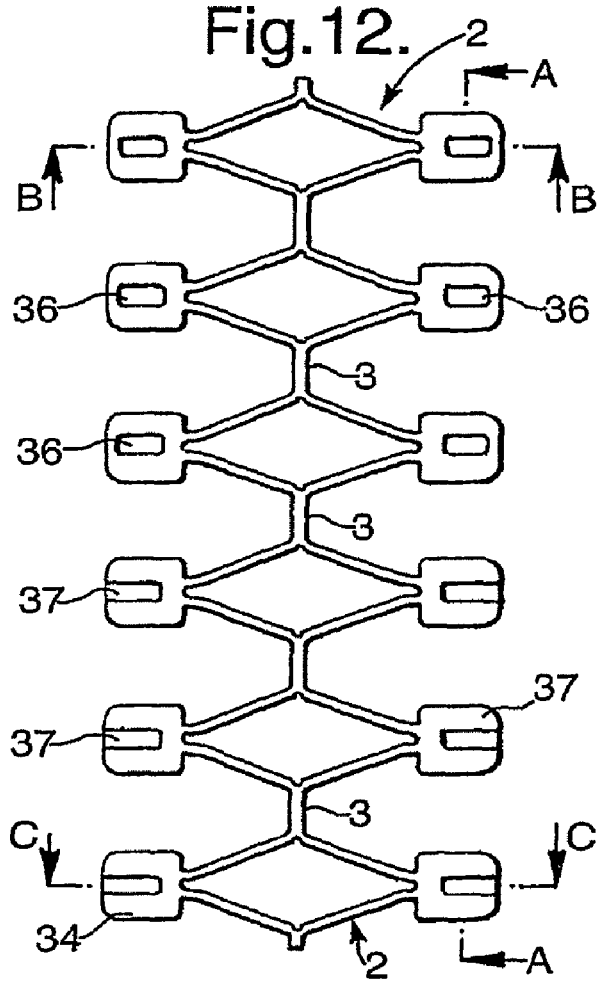
Figure 12B:
Figure 12C:
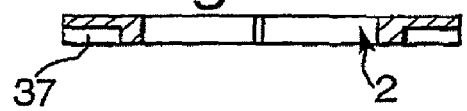
Figure 13:
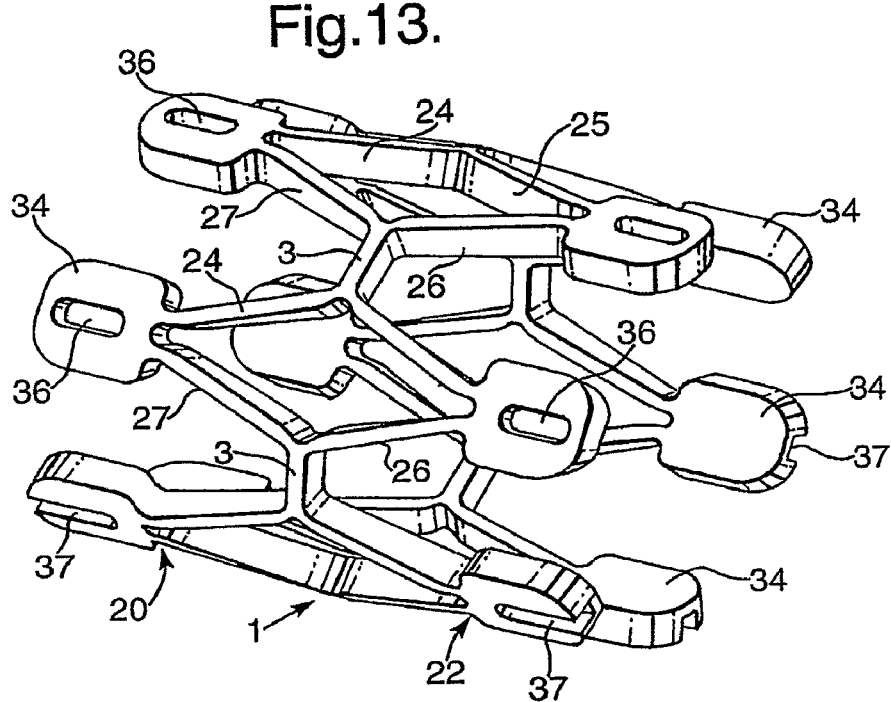
Figure 14:
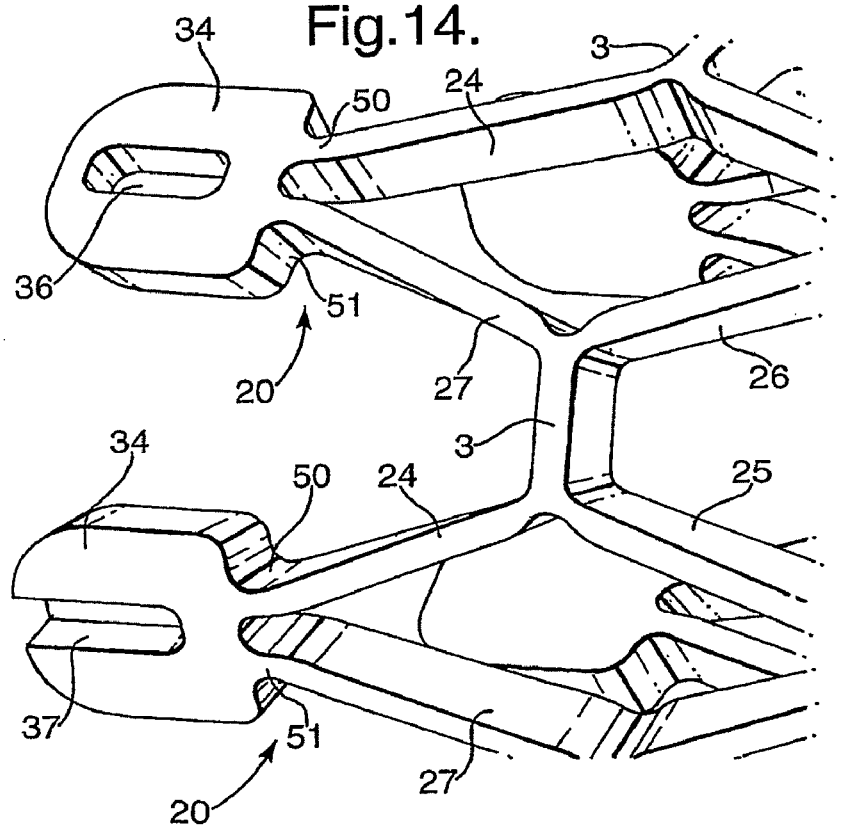
Figure 16:
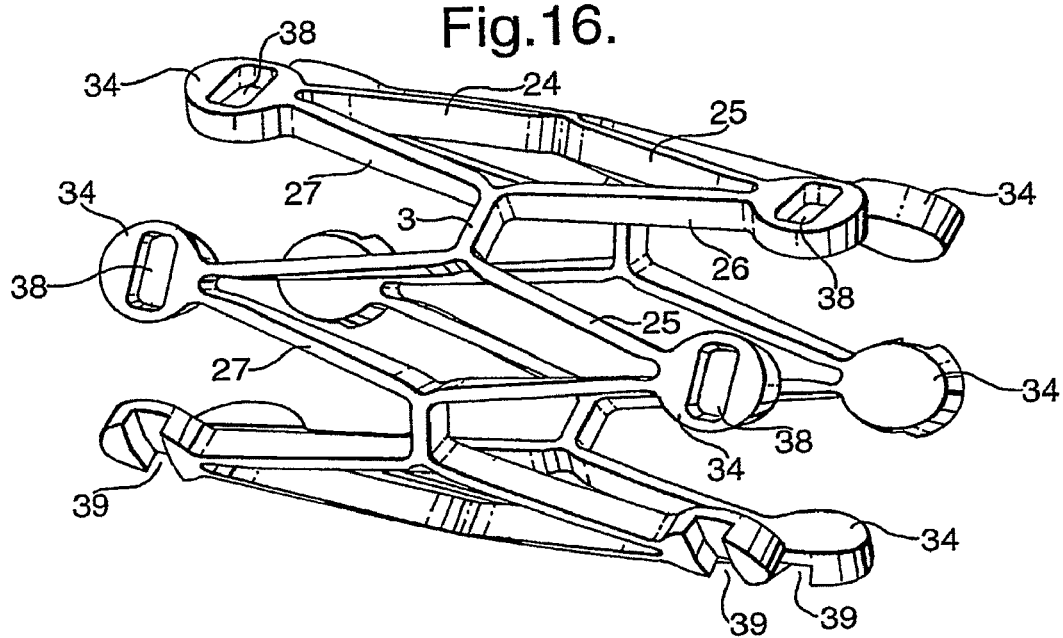
Figure 17:
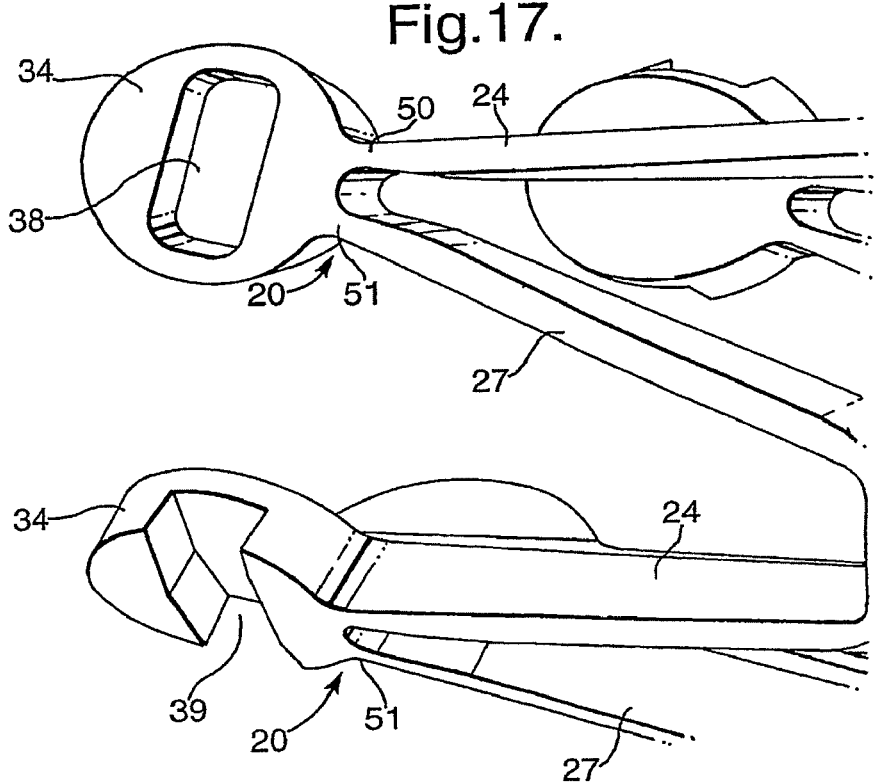
Figure 22:
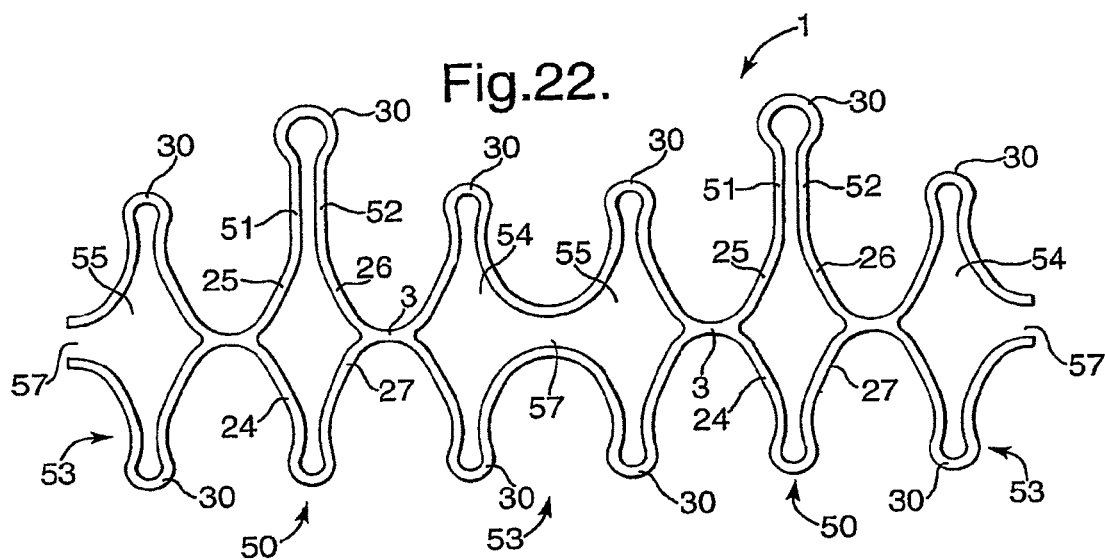
Figure 23:
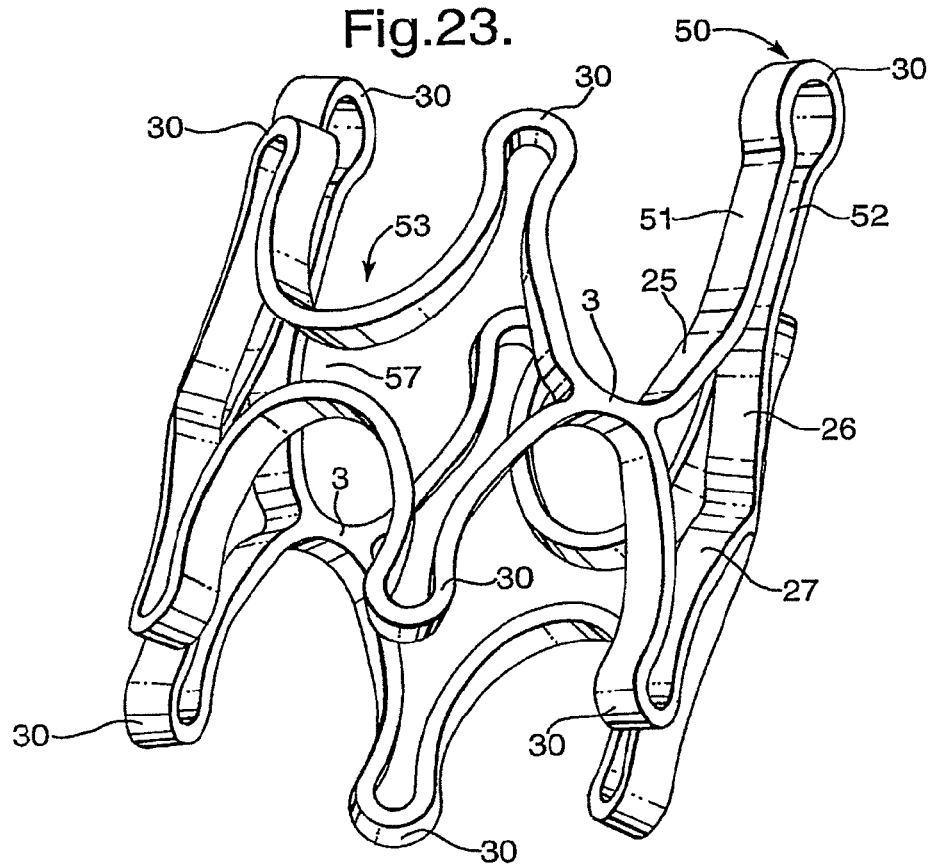

FIGS. 4A and B are side and perspective views of the stent of FIG. 1, but in which the number of elements is just three, in its "as cut" condition;

FIG. 5 is a perspective view of a single tubular element from the stent of FIG. 1;

FIGS. 6 and 7 are views similar to FIGS. 4A and 4B respectively, but showing the stent in the crimped condition;

FIGS. 8 and 9 are views similar to FIGS. 4A and 4B respectively, but showing the stent in the expanded condition;

FIGS. 10 and 11 are views similar to FIG. 4B, but showing two further embodiments showing both the first and second aspect of the invention;

FIG. 12 is a view similar to FIG. 2 showing a still further embodiment of the invention;

FIGS. 12A, B and C are views on the lines A-A, B-B and C-C respectively of FIG. 12;

FIG. 13 is a view similar to that of FIG. 5, but showing the embodiment of FIG. 12;

FIG. 14 is an enlarged view of part of FIG. 13;

FIG. 15 is a view similar to FIG. 2 showing a still further embodiment of the invention;

FIGS. 15A and B are views on the lines A-A and B-B respectively of FIG. 15;

FIG. 16 is a view similar to that of FIG. 5, but showing the embodiment of FIG. 15;

FIG. 17 is an enlarged view of part of FIG. 16;

FIG. 18 is a view similar to FIG. 2 showing a still further embodiment of the invention;

FIG. 18A is a view on the line A-A of FIG. 18;

FIG. 19 is a view similar to that of FIG. 5, but showing the embodiment of FIG. 18;

FIG. 20 is a view similar to FIG. 2 showing a still further embodiment of the invention;

FIG. 21 is a view similar to FIG. 5, but showing the embodiment of FIG. 20;

FIG. 22 is a view similar to FIG. 2 showing a still further embodiment of the invention;

FIG. 23 is a view similar to FIG. 5, but showing the embodiment of FIG. 22; and

Figure 24:
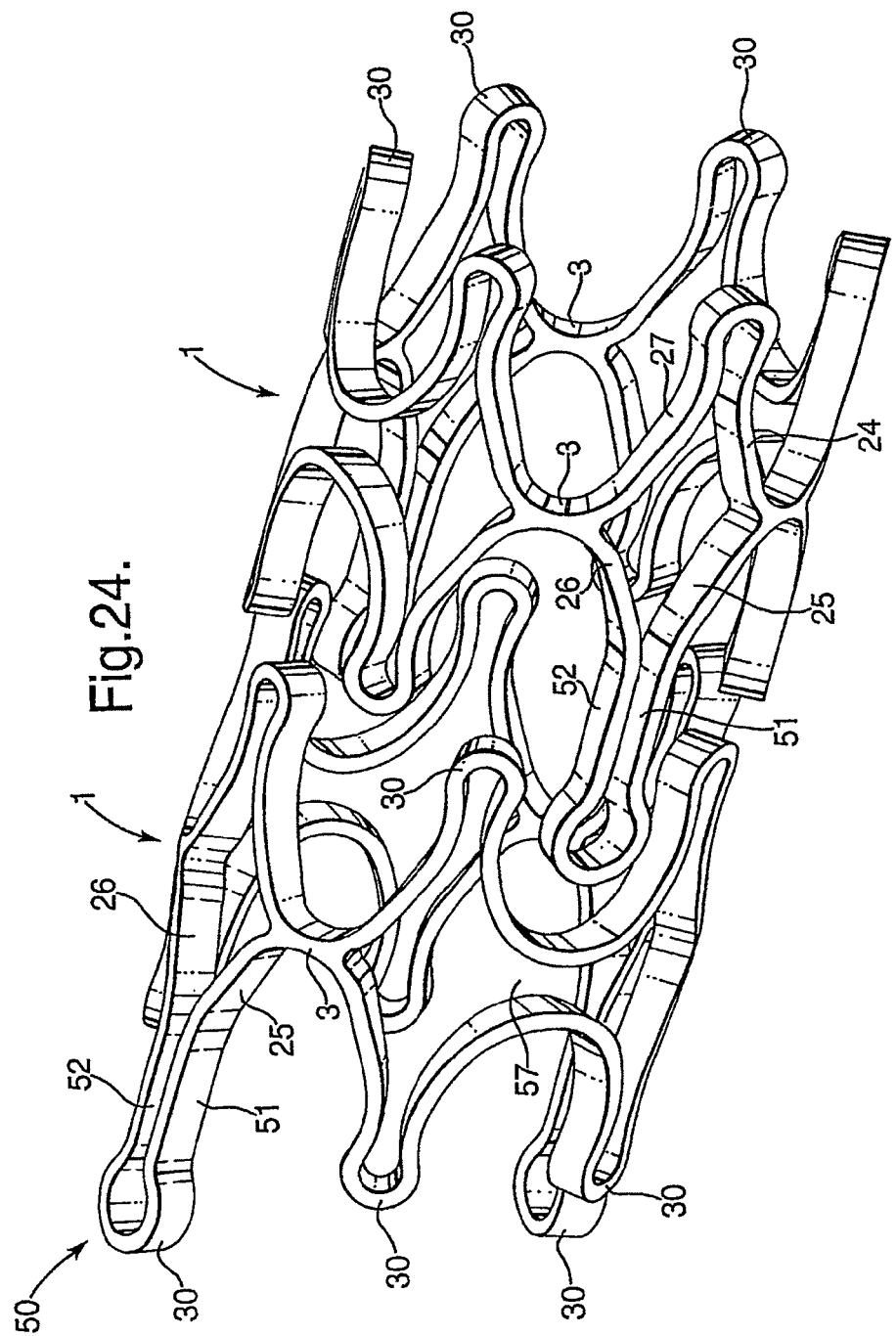

FIG. 24 is a view similar to FIG. 4b, but showing the embodiment of FIG. 22.

Referring firstly to FIGS. 1 and 4, the stent comprises a series of radially expandable tubular elements 1 aligned along a common longitudinal axis. Both of these Figures show the stent in its "as cut" condition by which is meant the condition in which it comes out of the manufacturing process. FIG. 1 illustrates the stent folded out in two dimensions, illustrated by the X-Y coordinates printed to the side of the drawing. In practice the stent is, of course, a three dimensional object, as illustrated in elevation and in perspective in FIGS. 4A and 4B respectively; thus it is assumed that the ends 12, 13 of each tubular element in FIG. 1 are in fact joined so that each element forms a closed loop of generally tubular configuration. In this description the longitudinal direction of the stent is parallel to the X-axis illustrated in FIG. 1, while the circumferential direction of the stent is parallel to the Y-axis in FIG. 1.

It will be noted that the tubular elements 1 are separate from one another in the sense that there is no direct physical link between them, keeping the tubular elements 1 in position. Instead alternative means are used to maintain the structural integrity of the stent. This will be explained in more detail below.

In the stent illustrated, all of the tubular elements are identical in structure and size although, as mentioned above, this need not necessarily be the case. A single tubular element 1 is shown, in two dimensional form in FIG. 2, and in three dimensional form in FIG. 5. Each tubular element comprises a plurality of closed cell elements 2 equally spaced apart by circumferentially extending linking members 3. In the embodiment illustrated each tubular element 1 comprises six closed cell elements 2, spaced apart circumferentially by 60°, but other numbers of closed cell elements are possible, according to the circumstances.

Figure 3:
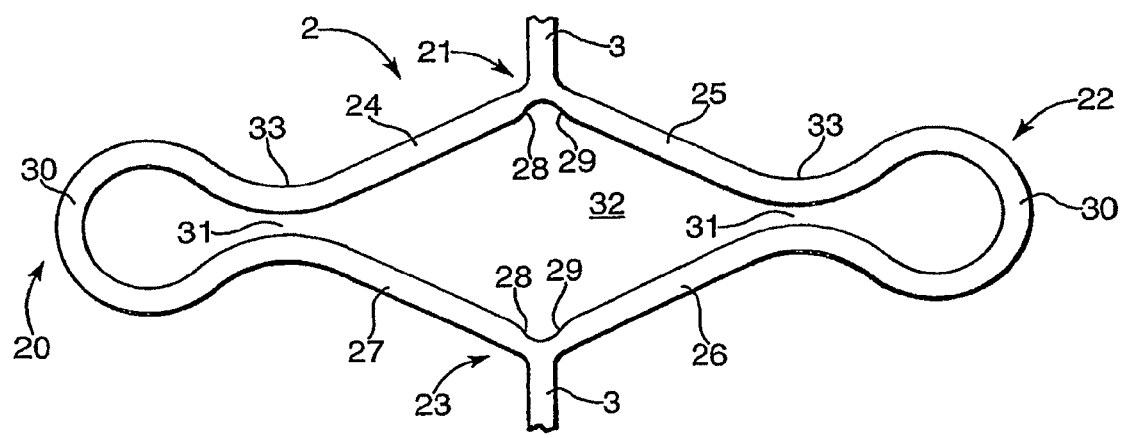
FIG. 3 is an enlarged view of one of the closed cell elements in the embodiment of FIG. 1.

A single closed cell element 2 is shown in enlarged detail in FIG. 3. The closed cell element has a generally rhombic or diamond shape defined by four side members 24 to 27 joined together by respective hinge members 20 to 23. The circumferential linking members 3 attached to respective opposite hinge members 21, 23.

The hinge members 21, 23 are formed by narrowed sections 28, 29 where the respective side members 24/27, 25/26 join the respective linking member 3. The hinge members 20, 22 are formed as a loop 30 having a narrowed opening 31 into the interior 32 of the cell element. This narrowed opening 31 corresponds to a waisted portion 33 which cooperates in the interlocking of individual tubular elements 1, as will be explained below.

Before the stent is used, it will generally be crimped to the balloon which will carry it to the treatment site and subsequently expand it. The crimping process involves compressing the "as cut" stent onto the balloon so that it is securely gripped. During compression the diameter of the tubular elements, decreases and this is achieved by a deformation of the closed cell elements 2 in such a way as to tend to close the elements up—i.e. so that the hinge members 21 and 23 move towards one another, thus reducing the circumferential length of the tubular element 1. During this process the closed cell elements bend at the hinge members 20 to 23. The crimped condition of the stent is illustrated in FIGS. 6 and 7 and since, in effect, the stent is expanded from this condition, the crimped condition can also be regarded as the unexpanded condition of the stent.

It will be noted in FIGS. 6 and 7 that, in the crimped condition of the stent, the hinge members 20, 22 belonging to adjacent tubular elements are interlocked, thus maintaining the structural integrity of the stent as a whole. This interlocking is achieved by the cooperating interlocking shapes of the hinge members 20, 22 in which each of the enlarged loops 30 lie between a pair of waisted portions 33 belonging to circumferentially adjacent closed cell elements 2 belonging to the same tubular element 1. By careful design, the closed cell elements can be configured to grip one another to maintain the shape of the stent so that it is not dislodged or deformed during its often long and tortuous passage to the treatment site. The longitudinal flexibility of the stent is ensured in the crimped condition by the fact that each loop 30 is allowed to move longitudinally a short but controlled distance towards the adjacent linking member 3. Thus, as the stent is bent longitudinally the loops 30 on one side move slightly, as described, whilst those on the other side move in the opposite direction. In an alternative embodiment (not shown) still greater longitudinal flexibility can be achieved by arranging that the elements are interlocked in such a way as to allow the loops to move, in a controlled manner, in either longitudinal direction.

When the stent reaches the treatment site, and the physician is satisfied as to its correct position, the balloon carrying the stent is expanded, in the known manner, to expand the stent from its condition shown in FIGS. 6 and 7 to its dilated condition shown in FIGS. 8 and 9. During this expansion process, the closed cell element 2 deform to a final shape clearly illustrated in FIG. 8. It will be seen that the hinge members 21, 23 have moved apart in the circumferential direction, thus increasing the circumferential length of each tubular element 1. At the same time, the hinge members 20, 22 of adjacent closed cell elements 2 move apart in the circumferential direction thus releasing the grip which they had previously exerted on the corresponding members of adjacent tubular elements. The stent however by now is supported both from within and without and so maintains its structural shape, even though the interlocking is released. The support from within comes from the balloon which is being internally pressurised to expand the stent; the support from without comes from the wall of the vessel being treated.

It will also be noted that, during expansion, the length, in the longitudinal direction of the stent, of each of the closed cell elements 2 reduces and this effect, in a stent with linking members between adjacent tubular elements, causes the overall length of the stent to reduce. This reduction in length is undesirable for various reasons, and it will be seen that the use of independent tubular elements 1 substantially eliminates this problem.

FIGS. 10 and 11 show modified versions of the stent of FIG. 1 in which the hinge members 20, 23 are modified from the open loop form described previously.

The stents of FIGS. 10 and 11 differ from that of FIG. 1 in that the hinge members 20, 22 comprise a block 34 of material from which the side members 24/27 and 25/26 emerge, via a respective narrowed portion to act as a hinge. Thus, in this case the hinge members 20, 22 each comprise a pair of hinges by which the respective side members 24/27 and 25/26 are attached to the blocks 34. Preferably these blocks 34 are formed integrally with the remainder of the tubular element, and are of the same material.

The difference between the embodiments of FIGS. 10 and 11 is in the shape of the blocks 34 which in the case of FIG. 10 is substantially rectangular and in the case of FIG. 11 is substantially circular. In both cases, each block 34 acts as an enlarged end in a similar manner to loop 30 of the FIG. 1 embodiment, and defines a narrowed waist portion where it joins the adjacent side members. The arrangement is thus able to interlock the individual tubular elements 1 in the same way as described above.

The advantages of a stent with independent tubular elements over one in which the tubular elements are linked by linking members can be summarised as follows:

1) Manufacture is made easier because only a basic tubular element has to be cut. Any stent length can readily be created by adding the appropriate number of tubular elements at the commencement of the assembly or crimping process.

2) The crimped stent has a high degree of longitudinal flexibility since it is not restrained by the inter-element linking members of known stents.

3) The crimped stent has a high degree of longitudinal conformability due to its tubular elements being interlocked at multiple cell locations.

4) There is substantially no shortening of the stent during expansion because the shortening of each tubular element does not affect the stent as a whole.

5) Once deployed, the stent has a high degree of longitudinal flexibility and of longitudinal and radial conformability due to the absence of the restraint imposed by inter-element linking members.

6) Once deployed the stent has a good vessel repartition and vessel scaffolding, with homogeneous support for the vessel wall—see particularly FIG. 8.

FIGS. 10 and 11 also illustrate the use of wells for containing therapeutic agent. It will be seen that, in each of FIGS. 10 and 11 the blocks 34 have formed on their exterior surface a well 35 which is intended to act as a reservoir for a therapeutic agent. Each well 35 takes the form of a shallow blind hole which opens into the exterior surface which, when the stent is deployed faces the wall of the vessel being treated.

Thus, any therapeutic agent contained within the wells 35 acts directly on the wall of the vessel, and is not substantially affected by the flow of fluid within the vessel.

Although only a single well 35 is formed in each block 34, it is possible for multiple smaller wells to be formed, perhaps each containing different drugs. Different drugs can be supplied on different tubular elements, making it easy to create a stent, as needed, containing an appropriate recipe of drugs.

The holes making up the wells 35 can be formed as through-holes, and plugged from the interior side to create a blind hole. Alternatively, the through hole can be left, and a suitable substance which will resist the washing away of the drug contained within the well can be deposited at the inner end of the through hole.

Although the wells 35 are shown as circular holes, it will be understood that other shapes are possible, including multi-sided, square or rectangular. Alternatively, the wells can be formed as grooves or slots opening into the exterior surface of the block 34.

The wells may additionally or instead of be provided at other locations, such as on the side members 24 to 27 of the closed cell elements 2. However, for this purpose, the side members would have to be made less deformable than they might otherwise be since any deformation of the reservoir during stent crimping or deployment might result in delamination of the reservoir contents, which would be undesirable. The blocks 34 are seen as attractive since they suffer substantially less deformation than other parts of the stent because their bulk, relative to the remaining components of the stent, is such that they are relatively stiff.

FIGS. 12 to 19 illustrate further embodiments similar to that of FIGS. 10 and 11, showing alternative arrangements of wells.

In the embodiment shown in FIGS. 12 to 14, two shapes of wells are shown. Half of the wells 35 have the shape of a short slot 36 which opens only into the exterior surface of the tubular element; the other half of the wells 35 have the shape of a slot 37 which opens both into the exterior surface of the tubular element 1, but also into the edge of the tubular element 1. Various combinations of these shaped wells can be used.

The enlarged view of FIG. 14 is of interest in that it clearly shows the structure of the left-hand hinge member 20. This can be seen to comprise two narrowed (i.e. less wide) portions 50, 51 where the respective side members 24 and 27 join the block 34.

In the embodiment of FIGS. 15 to 17, there is again a combination of different well shapes: a first type of well 35 formed of a short slot 38 extending in the circumferential direction of the stent; a second type of well 35 formed of a slot 39 which extends right across the block 34 in the circumferential direction of the stent, and is open at both ends.

FIGS. 18 and 19 show an embodiment in which again two different styles of well 35 are shown. On the left hand side: a block 40 is formed within the loop 30 of a hinge member of the type described above in relation to the embodiment of FIG. 1. The block 40 is formed with a well 35 formed as a blind hole, in a similar manner to the wells 35 of the embodiment of FIG. 11.

On the right hand side a block 41 is formed outside of the loop 30 and, once again, is equipped with a well 35 in the form of a blind hole. Since there is room beyond the hinge members 20, 22, the block 41 does not interfere with the interlocking of the tubular element 1 together during crimping, as described above.

The advantages of stents incorporating wells, as described above, can be summarised as follows:

1) The well can hold drugs without the need for a polymer matrix coating. The use of wells can eliminate coating delamination during stent deployment, thus reducing the risk of thrombosis.

2) The absence of a polymer matrix coating eliminates any potential biocompatibility problems arising from their use.

3) Once the stent is fully deployed, the outside surface of the stent is pushed against the wall of the vessel being treated; this means that the well is open only towards the vessel wall, to enable diffusion of the drugs into the vessel wall. In addition, the drug cannot be washed out by the flow of fluid in the vessel and so cannot have undesired effects elsewhere.

4) Compared to a thin (0.1-5 micron) drug layer coated on the stent, the reservoir can be loaded with a high dose and long life time.

5) The reservoir dimensions (diameter, length, width, depth) can be readily varied to the particular circumstances such as blood flow direction and drug release kinetics.

6) Each well can contain a single drug and therefore different drugs can be individually held in different wells without the danger of their reacting with each other.

FIGS. 20 to 24 show two further embodiments in which the closed cell elements in each tubular element 1 are not all identical, and in which the locating means are not provided on every closed cell element.

Referring to FIGS. 20 and 21, there is shown an embodiment in which each tubular element 1 is made up of two different shapes of closed cell element which alternate around the tubular element. The first shape of closed cell element, illustrated under reference 50 is similar to that of the closed cell elements described above with reference to FIG. 3, except that the loops 30 on one side of the rhombic shaped structure are positioned at the end of a pair of extended arms 51, 52. As a result these "extended" loops 30 protrude, in the axial direction of the stent, with respect to the remaining parts of the tubular element 1, and are thus able to interlock with the next adjacent tubular element.

FIGS. 22 to 24 illustrate an embodiment similar to that of FIGS. 20 and 21 but in which the extended loops 30 are open at their neck, as distinct from the arrangement in FIGS. 20 and 21, where each extended loop 30 takes the form of a closed ring which is attached at the ends of the arms 51, 52.

In both embodiments, the closed cell elements between the elements 50 are of different shape to the elements 50. These elements, given the reference 53, each comprise two rhombic-shaped sections 54, 55 which are joined by a narrow open neck portion 57.

The joining of adjacent tubular elements is shown in FIG. 24. FIG. 24 actually shows the embodiment of FIGS. 22 and 23, but it will be understood that the same interlocking technique can be used for the embodiment of FIGS. 20 and 21. In relation to FIG. 24, it should also be noted that the drawing shows the tubular elements in their expanded state—i.e. in a state in which they would not ordinarily be interlocked—see above.

The aperture 56 formed within the loop 30 in the embodiment of FIGS. 20 and 21 could be used as a well for containing a therapeutic, agent, in the manner described above. For this purpose, the aperture 56 may be a through aperture, plugged at its inner end, or may be a blind bore, opening into the outer surface only.

The stent which has been described is expandable between an unexpanded state (in practice, probably the crimped condition mentioned 10 above), in which it is able to be guided inside the lumen through a body duct, such as a blood vessel, for example, and an expanded state, in which the stent, after a uniform expansion, comes into contact with the inner wall of the body duct, defining a passage of approximately constant diameter inside said duct.

The stent will generally be forcibly expanded mechanically under the action of a force exerted radially outwards, for example under the effect of the inflation of a balloon. However, the stent may be of the "auto-expandable" type, i.e. capable of changing by itself from a first, unexpanded condition under stress, enabling it to be guided through the body duct, to a second, expanded, working condition.

The stent may be made of any material compatible with the body duct and the body fluids with which it may come into contact.

In the case of an auto-expandable stent, it will be preferable to use a material with a recovery capacity, for example, stainless steel, Phynox® or nitinol.

In the case of a stent utilising a forced expansion, a material with a low elastic recovery capacity may be used to advantage. Examples are metallic materials such as tungsten, platinum, tantalum, gold, or stainless steel.

The tubular elements 1 may be manufactured from a hollow tube with an approximately constant thickness corresponding to the desired thickness. The shape of the tubular elements may be formed either by laser cutting followed by electrochemical polishing, or by chemical or electrochemical treatment.

The tubular elements may alternatively be manufactured from a sheet of approximately constant thickness corresponding to the desired thickness of the stent. The geometric configuration of the tubular elements can be obtained either by laser cutting followed by electrochemical polishing, or by chemical or electrochemical treatment. The sheet cut in this way is then rolled up to form a cylinder and welded to give the desired final structure.

After assembly of the tubular elements 1 into a stent of the desired length, the stent can be deployed in a manner known per se. In the case of a stent utilising mechanically forced expansion, the insertion system will preferably comprise a balloon catheter onto which the stent will be crimped 15 in the unexpanded state before being introduced into an insertion tube for guiding it to the site to be treated.

The stent of the invention can be intended for both temporary or permanent placement in the duct or vessel to be treated.

What is claimed is:

1. A stent comprising:
   a tubular body made up of a plurality of separate, radially expandable, tubular elements aligned along a common longitudinal axis, each tubular element being physically unconnected to any other tubular element when the tubular elements are radially expanded,
   wherein at least some of the tubular elements each comprise a plurality of closed cell elements, each closed cell element joined to a circumferentially-adjacent closed cell element by a circumferentially-extending linking member, each circumferentially-extending linking member being attached to two circumferentially-neighboring closed cell elements at respective spaced apart attachment points,
   wherein each closed-cell element comprises a pair of side members narrowing inwardly towards a side hinge to form a waist portion,
   wherein at least some of the closed cell elements comprise an inter-engaging element engageable with a corresponding inter-engaging element on an adjacent tubular element holding the adjacent tubular elements together when engaged, at least in an unexpanded condition of the stent,
   wherein the inter-engaging element comprises the pair of side members narrowing inwardly towards side hinge forming the waist portion such that two waist portions on circumferentially adjacent closed cell elements act together to retain the corresponding inter-engaging element on the adjacent tubular element;
   wherein corresponding inter-engaging elements are movable relative to each other along the longitudinal axis when engaged allowing longitudinal movement between adjacent interlocked adjacent tubular elements so as to allow for increased flexibility of the stent in the unexpanded configuration and reduce shortening of the stent during expansion.

2. A stent as claimed in claim 1 wherein the tubular elements are also compressible.

3. A stent as claimed in claim 1 wherein each closed cell element is expandable in the circumferential direction of the tubular element, thus allowing the tubular element to expand and contract.

4. A stent as claimed in claim 3 wherein each closed cell element is positioned symmetrically with respect to the circumferential linking members.

5. A stent as claimed in claim 3 wherein each closed cell element comprises two attachment points, each of which joins to a respective circumferential linking member, and wherein the closed cell element is capable of expanding from a first position in which the attachment points are a first distance apart, to a second position in which the attachment points are a second distance apart, wherein the first distance is less than the second distance.

6. A stent as claimed in claim 5 wherein, between said attachment points, each closed cell element comprises proximal and distal members, spaced apart from each other in the direction of the longitudinal axis, said proximal and distal members being capable of bending to accommodate the expansion from the first position to the second position, wherein the proximal and distal members include the side members in each respective closed cell element.

7. A stent as claimed in claim 6 wherein the plurality of closed cell element comprises circumferentially spaced end hinge members joining the proximal and distal members of each closed cell element, wherein an end of the proximal and distal members of each closed cell element are joined together at a respective end hinge member.

8. A stent as claimed in claim 7 wherein each end hinge member is attached at one end of a respective circumferentially-extending linking member, the other end of the linking member having attached thereto the opposite end hinge member of the next adjacent closed cell element.

9. A stent as claimed in claim 6 wherein each of the proximal and distal members comprises a flexible member joining the attachment points.

10. A stent as claimed in claim 6 wherein each of the proximal and distal members comprises two or more relatively rigid side members joined by the side hinge.

11. A stent as claimed in claim 1 wherein said side members together form the shape of a rhombus.

12. A stent as claimed in claim 1 wherein each of said side members is of rectilinear shape.

13. A stent as claimed in claim 1 wherein all of the closed cell elements making up each tubular element are of the same shape.

14. A stent as claimed in claim 1 wherein some of the closed cell elements making up each tubular element are of a different shape to the remainder.

15. A stent as claimed in claim 1 wherein an exterior surface of the tubular body is equipped with wells which open onto the exterior surface, said wells being suitable to contain one or more therapeutic agents.

16. A stent as claimed in claim 15 in which the wells comprise holes or grooves opening into the exterior surface of the stent.

17. A stent as claimed in claim 16 wherein the holes or grooves are blind, such that the holes or grooves do not pass completely through the material of the stent.

18. A stent as claimed in claim 16 wherein the holes or grooves pass through to an interior of the stent.

19. A stent as claimed in claim 18 in which an inner end of the hole or groove is plugged by a material which prevents or considerably reduces the flow of a therapeutic agent therethrough.

20. A stent as claimed in claim 19 wherein said material contains a therapeutic agent.

21. A stent as claimed in claim 15 wherein the closed cell elements are formed with blocks on each of which are formed one or more of said wells.

22. A stent as claimed in claim 15 wherein at least some of said wells contain multiple therapeutic agents arranged in layers so as to release in sequence.

23. A stent as claim in claim 1, wherein the inter-engaging elements of adjacent tubular elements are configured to engage one another so as to interlock adjacent stents in the unexpanded configuration and are dis-engaged in the expanded configuration so as to inhibit shortening of the stent during expansion.

* * * * *